(12) United States Patent
Wicha et al.

(10) Patent No.: US 8,435,746 B2
(45) Date of Patent: May 7, 2013

(54) ALDEHYDE DEHYDROGENASE 1 (ALDH1) AS A CANCER STEM CELL MARKER

(75) Inventors: Max S. Wicha, Ann Arbor, MI (US); Gabriela Dontu, Ann Arbor, MI (US); Christophe Ginestier, Ann Arbor, MI (US); Emmanuelle Charafe-Jauffret, Marsielle (FR); Suling Liu, Ann Arbor, MI (US)

(73) Assignee: The Regents of the University of Michigan, Ann Arbor, MI (US)

( * ) Notice: Subject to any disclaimer, the term of this patent is extended or adjusted under 35 U.S.C. 154(b) by 172 days.

(21) Appl. No.: 12/830,993

(22) Filed: Jul. 6, 2010

(65) Prior Publication Data
US 2010/0291581 A1 Nov. 18, 2010

Related U.S. Application Data

(63) Continuation of application No. 11/859,901, filed on Sep. 24, 2007, now abandoned.

(60) Provisional application No. 60/846,648, filed on Sep. 22, 2006.

(51) Int. Cl.
*G01N 33/53* (2006.01)
*A01N 61/00* (2006.01)

(52) U.S. Cl.
USPC .............................................. 435/7.1; 514/1

(58) Field of Classification Search ............... None
See application file for complete search history.

(56) References Cited

U.S. PATENT DOCUMENTS

| | | | |
|---|---|---|---|
| 5,225,539 | A | 7/1993 | Winter et al. |
| 6,004,528 | A | 12/1999 | Bergstein |
| 6,984,522 | B2 | 1/2006 | Clarke et al. |
| 6,991,897 | B2 | 1/2006 | Smith et al. |
| 7,115,360 | B2 | 10/2006 | Clarke et al. |
| 2005/0089518 | A1 | 4/2005 | Clarke et al. |
| 2005/0232927 | A1 | 10/2005 | Clarke et al. |
| 2006/0019256 | A1 | 1/2006 | Clarke et al. |
| 2007/0099209 | A1 | 5/2007 | Clarke et al. |
| 2007/0105133 | A1 | 5/2007 | Clarke et al. |
| 2007/0220621 | A1 | 9/2007 | Clarke et al. |
| 2007/0231325 | A1 | 10/2007 | Clarke et al. |
| 2007/0243192 | A1 | 10/2007 | Wicha et al. |
| 2008/0019961 | A1 | 1/2008 | Wicha et al. |
| 2008/0064049 | A1 | 3/2008 | Clarke et al. |

FOREIGN PATENT DOCUMENTS

| | | |
|---|---|---|
| WO | 02/12447 | 2/2002 |
| WO | WO 03/050502 | 6/2003 |
| WO | 2005/005601 | 1/2005 |
| WO | 2005/074633 | 8/2005 |
| WO | 2006/138275 | 12/2006 |
| WO | 2007/053648 | 5/2007 |

OTHER PUBLICATIONS

Ikawa et al (JBC, 1983, 258(10): 6282-6287).*
Tockman et al (Cancer Res., 1992, 52:2711s-2718s).*
Seigel et al (Molecular Vision, 2005, 11: 729-737).*
Sladek et al (Cancer Chemother Pharmacol, 2002, 49: 309-321).*
Low et al (J. Clin Oncol, Oct. 2004, 22(20): 4067-4074).*
Kitahara et al (Neoplasia, 2002, 4: 295-303).*
Rose et al (J Virol Methods, 1991, 35(3): Abstract).*
Wicha et al., "Cancer Stem Cells: An Old Idea—A Paradigm Shift" Cancer Research, 2006, 66:1883-1890.
Dontu et al., "Stem Cells in Mammary Development and Carcinogenesis Implications for Prevention and Treatment," Stem Cell Reviews, 2005, 3(1):207-214.
Sophos et al., "Aldehyde dehydrogenase gene superfamily: the 2002 update," Chem. Biol. Interact, 2003, 5(22):143-144.
Duester et al., "Families of retinoid dehydrogenases regulating vitamin A function Production of visual pigment and retinoic acid," Eur J. Biochem., 2000, 267:4315-4324.
Glinsky et al., "Microarray analysis identifies a death-from cancer signature predicting therapy failure in patients with multiple types of cancer," J. Clin. Invest., 2005, 115(6):1503-1521.
Lahad et al., "Stem cell-ness: a "magic marker" for cancer," J. Clin Invest., 2005, 115(6):1463-1467.
Dontu et al., "In vitro propagation and transcriptional profiling of human mammary stem/progenitor cells" Gen. & Dev., 2003, 17(1): 1253-1270.
Kastan et al., "Direct demonstration of elevated aldehyde dehydrogenase in human hematopoietic progenitor cells," Blood, 1990, 75:1947-1950.
Gudjonsson et al., "epithelial cell line with stem cell properties Isolation, immortalization, and characterization of a human breast," Genes & Dev., 2002, 16:693-706.
Otterback et al., "Cytokevatin 5/6 immunohistochemistry assists the differential diagnosis of atypical proliferations of the breast," Histopathology, 2000 37(3):232-40.
Dontu et al., "Role of Notch signaling in cell-fate determination of human mammary stem/progenitor cells," Breast cancer research: BCR. (2004) 6(6).
Liu et al., "Hedgehog Signaling and Bmi-1 Regulate Self-renewal of Normal and Malignant Human Mammary Stem Cells," Cancer Res (2006) 66(12), 6063-6071.
Albertsen et al, "A physical map and candidate genes in the BRCA1 region on chromosome 17q12-21," Nature Genetics (1994) 7, 472-479.
Poole et al. "Prevention of Brca1-Mediated Mammary Tumorigenesis in ,Mice by a Progesterone Antagonist," Science (2006) 314(5804), 1467-1470.
Liu et al. "Somatic loss of BRCA1 and p53 in mice induces mammary tumors with features of human BRCA1-mutated basal-like breast cancer," PNAS (2007)104, 12111-12116.
Turner et al., "Basal-like breast cancer and the BRCA1 phenotype," Oncogene (2006) 25(43), 5846-5853.
Dontu et al. Stem cells in normal breast development and breast cancer. Cell Proliferation. 4 and 16 Oct. 2003, vol. 36, No. s1, pp. 59-72; p. 62, para 1 and 2 and Fig 1; p. 67, para 3.
Foulkes, "BRCA1 functions as a breast stem cell regulator," Journal of Medical Genetics. Jan. 6, 2005, vol. 41 pp. 1-5: p. 2, col. 1; p. 4, col. 1, and the abstract.
Meyn et al. Induction of apoptosis in murine tumors by cyclophosphamide. Cancer 12 Chemotherapy and Pharmacology. Sep. 1994, vol. 33 No. 5 pp. 410-414; abstract.

(Continued)

*Primary Examiner* — Sean Aeder
(74) *Attorney, Agent, or Firm* — Casimir Jones, S.C.

(57) ABSTRACT

The present invention relates to compositions and methods for treating, characterizing, and diagnosing cancer. In particular, the present invention provides a novel stem cell cancer marker, ALDH1, useful for the diagnosis, characterization, and treatment of solid tumor stem cells.

7 Claims, 27 Drawing Sheets

OTHER PUBLICATIONS

American Joint Committee on Cancer: AJCC Cancer Staging Manual. Philadelphia, Pa.: Lippincott-Raven Publishers, 5th ed., 1997, pp. 171-180.

Harris, J R, "Staging of breast carcinoma" in Harris, J. R., Hellman, S., Henderson, I. C., Kinne D. W. (eds.): Breast Diseases. Philadelphia, Lippincott, 1991.

Morrison et al., "Regulatory Mechanisms in Stem Cell Biology," Cell 88(3): 287-98 (1997).

Morrison et al., "Hematopoietic stem cells: challenges to expectations," Curr. Opin. Immunol. 9(2): 216-21 (1997).

Morrison et al., "The Biology of Hennatopoietic Stem Cells," Annu. Rev. Cell. Dev. Biol. 11: 35-71 (1995).

Pandis et al., "Cytogenetic Comparison of Primary Tumors and Lymph Node Metastases in Breast Cancer Patients," Genes, Chromosomes & Cancer 22:122-129 (1998).

Kuukasjrvi et al., "Genetic Heterogencity and Clonal Evolution Underlying Development of Asynchronous Metastasis in Human Breast Cancer," Cancer Res. 57: 1597-1604 (1997).

Bonsing et al., "High Levels of DNA Index Heterogeneity in Advanced Breast Carcinomas,"Cancer 71: 382-391 (1993).

Bonsing et al., "Allelotype Analysis of Flow-Sorted Breast Cancer Cells Demonstrates Genetically Related Diploid and Aneuploid Subpopulations in Primary Tumors and Lymph Node Metastases," Genes Chromosomes & Cancer 28: 173-183 (2000).

Beerman, H et al., "Flow Cytometric Analysis of DNA Stemline Heterogeneity in Primary and Metastatic Breast Cancer," Cytometry. 12(2): 147-54 (1991).

Aubele M & Werner M, "Heterogeneity in breast cancer and the problem of relevance of findings," Analyt. Cell. Path. 19: 53 (1999).

Shen et al., "Genome-wide Search for Loss of Heterozygosity Using Laser Capture Microdissected Tissue of Breast Carcinoma: An Implication for Mutator Phenotype and Breast Cancer Pathogenesis," Cancer Res. 60: 3884 (2000).

Kuperwasser et al., "Reconstruction of functionally normal and malignant human breast tissues in mice," PNAS, 101:4966-71, 2004.

Van Golen, KL, et al., "A Novel Putative Low-Affinity Insulin-like Growth Factor-binding Protein, LIBC (Lost in Inflammatory Breast Cancer), and RhoC GTPase Correlate with the Inflammatory Breast Cancer Phenotype," Clin. Cancer Res. 5, 2511-2519 (1999).

Minn et al., "Lung metastasis genes couple breast tumor size and metastatic spread," Proc.Natl.Acad.Sci.U.S.A, 104, 6740-6745 (2007).

Shackleton, et al., "Generation of a functional mammary gland from a single stem cell,"(2006) Nature 439 (7072), 84-88.

Low et al., "Long-term follow-up for locally advanced and inflammatory breast cancer patients treated with multimodality therapy," J Clin Oncol, 2004, 22(20):4067-4074.

Sladek et al., "Cellular levels of aldehyde dehydrogenases (ALDH1A1 and ALDH3A1) as predictors of therapeutic responses to cyclophosphamide-based chemotherapy of breast cancer: a retrospective study," Cancer Chemother Pharmacol, 2002, 46:309-321.

Seigel et al., "Cancer stem cell charateristics in retinoblastoma," Molecular Vision, 2005, 11:729-737.

* cited by examiner

A

B

C

D

A

B

ALDEHYDE DEHYDROGENASE 1 (ALDH1) AS A CANCER STEM CELL MARKER

The present application claim is a continuation of pending U.S. patent application Ser. No. 11/859,901 filed Sep. 24, 2007, which claims priority to U.S. Provisional Application Ser. No. 60/846,648 filed Sep. 22, 2006, each of which is herein incorporated by reference.

This invention was made with government support under Grant No. R01-CA101860 awarded by the National Institutes of Health. The Government has certain rights in the invention.

FIELD OF THE INVENTION

The present invention relates to compositions and methods for treating, characterizing, and diagnosing cancer. In particular, the present invention provides a novel stem cell cancer marker, aldehyde dehydrogenase 1 (ALDH1), useful for the diagnosis, characterization, and treatment of solid tumor stem cells.

BACKGROUND OF THE INVENTION

Breast cancer is the most common female malignancy in most industrialized countries, as it is estimated to affect about 10% of the female population during their lifespan. Although its mortality has not increased along with its incidence, due to earlier diagnosis and improved treatment, it is still one of the predominant causes of death in middle-aged women. Despite earlier diagnosis of breast cancer, about 1-5% of women with newly diagnosed breast cancer have a distant metastasis at the time of the diagnosis. In addition, approximately 50% of the patients with local disease who are primarily diagnosed eventually relapse with the metastasis. Eighty-five percent of these recurrences take place within the first five years after the primary manifestation of the disease.

On presentation, most patients with metastatic breast cancer have only one or two organ systems involved. As the disease progresses over time, multiple sites usually become involved. Indeed, metastases can be found in nearly every organ of the body at autopsy. The most common sites of metastatic involvement observed are locoregional recurrences in the skin and soft tissues of the chest wall, as well as in axilla, and supraclavicular area. The most common site for distant metastasis is the bone (30-40% of distant metastasis), followed by lung and liver. Metastatic breast cancer is generally considered to be an incurable disease. However, the currently available treatment options often prolong the disease-free state and overall survival rate, as well as increase the quality of the life. The median survival from the manifestation of distant metastases is about three years.

Current methods of diagnosing and staging breast cancer include the tumor-node-metastasis (TNM) system that relies on tumor size, tumor presence in lymph nodes, and the presence of distant metastases as described in the American Joint Committee on Cancer: AJCC Cancer Staging Manual. Philadelphia, Pa.: Lippincott-Raven Publishers, 5th ed., 1997, pp 171-180, and in Harris, J R: "Staging of breast carcinoma" in Harris, J. R., Hellman, S., Henderson, I. C., Kinne D. W. (eds.): Breast Diseases. Philadelphia, Lippincott, 1991. These parameters are used to provide a prognosis and select an appropriate therapy. The morphologic appearance of the tumor can also be assessed but because tumors with similar histopathologic appearance can exhibit significant clinical variability, this approach has serious limitations. Finally assays for cell surface marker can be used to divide certain tumors types into subclasses. For example, one factor considered in the prognosis and treatment of breast cancer is the presence of the estrogen receptor (ER) as ER-positive breast cancers typically respond more readily to hormonal therapies such as tamoxifen than ER-negative tumors. Yet these analyses, though useful, are only partially predictive of the clinical behavior of breast tumors, and there is much phenotypic diversity present in breast cancers that current diagnostic tools fail to detect.

Traditional modes of cancer therapy include radiation therapy, chemotherapy, and hormonal therapy. Yet because of the difficulty in predicting the clinical course of early stage breast cancer from standard clinical and pathologic features, current practice is to offer systemic chemotherapy to most women even though the majority of these women would have good outcome in the absence of chemotherapy. Chemotherapy has severe side effects and itself carries a 1% mortality rate, and thus unnecessary suffering and deaths could be avoided if patients could be divided into high and low risk subgroups. Thus, there exists a need for improved methods to classifying tumors for better prognosis and treatment selection.

Furthermore, although current therapies can often prolong the disease-free state and overall survival when used on high-risk patients, they are limited by their lack of specificity and the emergence of treatment-resistant cancer cells. Approximately two thirds of people diagnosed with cancer will die of their cancer within five years. Thus there is a great call for the identification of additional genes that can serve as selective therapies for the treatment of cancer.

Colorectal cancer is the third most common cancer and the fourth most frequent cause of cancer deaths worldwide. Approximately 5-10% of all colorectal cancers are hereditary with one of the main forms being familial adenomatous polyposis (FAP), an autosomal dominant disease in which about 80% of affected individuals contain a germline mutation in the adenomatous polyposis coli (APC) gene. Colorectal carcinoma has a tendency to invade locally by circumferential growth and for lymphatic, hematogenous, transperitoneal, and perineural spread. The most common site of extralymphatic involvement is the liver, with the lungs the most frequently affected extra-abdominal organ. Other sites of hematogenous spread include the bones, kidneys, adrenal glands, and brain.

The current staging system for colorectal cancer is based on the degree of tumor penetration through the bowel wall and the presence or absence of nodal involvement. This staging system is defined by three major Duke's classifications: Duke's A disease is confined to submucosa layers of colon or rectum; Duke's B disease has tumors that invade through muscularis propria and can penetrate the wall of the colon or rectum; and Duke's C disease includes any degree of bowel wall invasion with regional lymph node metastasis.

Surgical resection is highly effective for early stage colorectal cancers, providing cure rates of 95% in Duke's A and 75% in Duke's B patients. The presence of positive lymph node in Duke's C disease predicts a 60% likelihood of recurrence within five years. Treatment of Duke's C patients with a post surgical course of chemotherapy reduces the recurrence rate to 40%-50%, and is now the standard of care for these patients. Because of the relatively low rate of reoccurrence, the benefit of post surgical chemotherapy in Duke' B has been harder to detect and remains controversial. However, the Duke's B classification is imperfect as approximately 20-30% of these patients behave more like Duke's C and relapse within five years. Thus there is a clear need to identify better prognostic factors for selecting Duke's B patients that are likely to relapse and would benefit from therapy.

During normal animal development, cells of most or all tissues are derived from normal precursors, called stem cells (Morrison et al., Cell 88(3): 287-98 (1997); Morrison et al., Curr. Opin. Immunol. 9(2): 216-21 (1997); Morrison et al., Annu. Rev. Cell. Dev. Biol. 11:35-71 (1995)). Stem cells are cells that: (1) have extensive proliferative capacity; 2) are capable of asymmetric cell division to generate one or more kinds of progeny with reduced proliferative or developmental potential; and (3) are capable of symmetric cell divisions for self-renewal or self-maintenance. In adult animals, some cells (including cells of the blood, gut, breast ductal system, and skin) are constantly replenished from a small population of stem cells in each tissue. The best-known example of adult cell renewal by the differentiation of stem cells is the hematopoietic system where developmentally immature precursors (hematopoietic stem and progenitor cells) respond to molecular signals to form the varied blood and lymphoid cell types.

Solid tumors are composed of heterogeneous cell populations. For example, breast cancers are a mixture of cancer cells and normal cells, including mesenchymal (stromal) cells, inflammatory cells, and endothelial cells. Classic models of cancer hold that phenotypically distinct cancer cell populations all have the capacity to proliferate and give rise to a new tumor. In the classical model, tumor cell heterogeneity results from environmental factors as well as ongoing mutations within cancer cells resulting in a diverse population of tumorigenic cells. This model rests on the idea that all populations of tumor cells would have some degree of tumorigenic potential. (Pandis et al., Genes, Chromosomes & Cancer 12:122-129 (1998); Kuukasjrvi et al., Cancer Res. 57: 1597-1604 (1997); Bonsing et al., Cancer 71: 382-391 (1993); Bonsing et al., Genes Chromosomes & Cancer 82: 173-183 (2000); Beerman H et al., Cytometry. 12(2): 147-54 (1991); Aubele M & Werner M, Analyt. Cell. Path. 19: 53 (1999); Shen L et al., Cancer Res. 60: 3884 (2000).).

An alternative model for the observed solid tumor cell heterogeneity is that solid tumors result from a "solid tumor stem cell" (or "cancer stem cell" from a solid tumor) that subsequently undergoes chaotic development through both symmetric and asymmetric rounds of cell divisions. In this stem cell model, solid tumors contain a distinct and limited (possibly even rare) subset of cells that share the properties of normal "stem cells", in that they extensively proliferate and efficiently give rise both to additional solid tumor stem cells (self-renewal) and to the majority of tumor cells of a solid tumor that lack tumorigenic potential. Indeed, mutations within a long-lived stem cell population can initiate the formation of cancer stem cells that underlie the growth and maintenance of tumors and whose presence contributes to the failure of current therapeutic approaches.

Although great strides have been made understanding the genetic changes that lead to cancer (e.g. breast cancer and colorectal cancer), the lack of reliable tumor assay for de novo human cancer cells has hindered the ability to understand the effects of these mutations at the cellular level. Also, the lack of identified cancer markers for solid tumor stem cells has hindered the development of diagnostics and therapeutics for cancer patients (e.g. breast cancer patients). As such, what is needed is a reliable tumor assay as well as the identification of cancer markers for solid tumor stem cells, preferably methods that allow in situ type detection (e.g., immunohistochemistry based methods that can be used on tissue samples).

SUMMARY OF THE INVENTION

The present invention relates to compositions and methods for treating, characterizing, and diagnosing cancer. In particular, the present invention provides a novel stem cell cancer marker, aldehyde dehydrogenase 1 (ALDH1), useful for the diagnosis, characterization, and treatment of solid tumor stem cells.

In some embodiments, the present invention provides methods of detecting solid tumor stem cells comprising; a) contacting a tissue sample with an antibody or antibody fragment or other specific ligand configured to detect ALDH1 expression in cells in the tissue sample; and b) determining if the tissue sample contains solid tumor stem cells based on the presence or absence of ALDH1 expression in the tissue sample. In particular embodiments, the method further comprises c) determining if the tissue sample contains low levels of BRCRA1 expression.

In certain embodiments, the present invention provides methods for identifying a cancer patient with a poor prognosis, comprising: a) obtaining a biological sample from the cancer patient comprising cancer cells; b) treating the biological sample to determine if a portion of the cancer cells are ALDH1 expressing solid tumor stem cells, and c) identifying the cancer patient as having a poor prognosis, wherein the identifying comprises demonstrating the presence of the ALDH1 expressing solid tumor stem cells in the biological sample.

In particular embodiments, the treating comprises contacting the biological sample with an antibody or antibody fragment specific for ALDH1. In other embodiments, the treating comprises contacting the biological sample with reagents configured for detecting expression of ALDH1 mRNA.

In further embodiments, the present invention provides methods of detecting solid tumor stem cells, comprising; a) providing a tissue sample from a subject, and b) detecting a stem cell cancer marker in the tissue sample under conditions such that the presence or absence of solid tumor stem cells in the tissue sample is determined, wherein the solid tumor stem cell marker comprises ALDH1.

In certain embodiments, the detecting comprises determining an expression level for the stem cell cancer marker. In further embodiments, the detecting comprises detecting mRNA expression of the stem cell cancer marker. In some embodiments, the detecting comprises detecting polypeptide expression of the stem cell cancer marker. In other embodiments, the subject comprises a human subject. In additional embodiments, the methods further comprise the step of c) providing a prognosis to the subject. In some embodiments, the sample comprises breast cancer cells (e.g., inflammatory breast cancer cells). In other embodiments, the sample comprises colon cancer cells. In further embodiments, the sample is a biopsy sample. In other embodiments, the sample is a paraffin embedded sample.

In some embodiments, the present invention provides methods for reducing the size of a solid tumor comprising contacting cells of a solid tumor with a biologically effective amount of a composition comprising at least one agent directed against a stem cell cancer marker, wherein the stem cells are cancer stem cells defined by ALDH1 expression.

In particular embodiments, the biologically effective amount is an amount sufficient to cause cell death of or inhibit proliferation of solid tumor stem cells in the solid tumor. In other embodiments, the at least one agent is an antibody, antibody fragment, peptide, anti-sense, siRNA, or small molecule specific for ALDH1. The nucleic acid sequence of ALDH1 is known in the art (NM_000689) and may be used to select anti-sense and siRNA type molecules using available technologies.

In certain embodiments, the present invention provides methods for killing or inhibiting the proliferation of solid tumor stem cells comprising contacting the solid tumor stem cells with a biologically effective amount of a composition comprising at least one agent targeted to ALDH1.

In some embodiments, the methods further comprise identifying the death of or the prevention of the growth of the solid tumor stem cells following the contacting. In particular embodiments, the cell death is apoptosis.

In other embodiments, the present invention provides an isolated solid tumor stem cell, wherein: (a) the solid tumor stem cell is derived from a solid tumor; (b) the solid tumor stem cell expresses ALDH1; and (c) the solid tumor stem cell is tumorogenic. In certain embodiments, the isolated solid tumor stem cell over-expresses ERB2. In particular embodiments, the isolated solid the solid tumor stem cell expresses the cell surface marker epithelial specific antigen (ESA). In certain embodiments, the solid tumor stem cell expresses the cell surface marker epithelial specific antigen (ESA) and CD10. In some embodiments, the solid tumor stem cell does not expresses the cell surface marker epithelial specific antigen (ESA) or CD10. In other embodiments, cancer stem cells is a breast cancer or an ovarian cancer. In additional embodiments, the solid tumor stem cell contains a heterologous polynucleotide vector. In further embodiments, the solid tumor stem cell forms a new tumor upon transplantation into a host animal. In some embodiments, the host animal is an immunocompromised animal (e.g., mouse). In certain embodiments, the methods further comprise a culture medium, in which culture medium the solid tumor stem cell is situated. In particular embodiments, the cell is capable of differentiation along both myoepithelial and luminal epithelial lineages.

In certain embodiments, the present invention provides methods for enriching a population of cells for solid tumor stem cells, comprising the steps of: (a) dissociating a solid tumor to form a cell suspension; (b) contacting the dissociated cells with at least one reagent, wherein the reagent selectively binds to ALDH1 protein; and (c) selecting cells that bind to the reagent that selectively binds, wherein the selected cells are enriched in tumor stem cells as compared with the unfractionated population of solid tumor cells. In particular embodiments, the solid tumor is a sarcoma or epithelial cancer. In some embodiments, the solid tumor cells are breast or colon tumor cells. In further embodiments, the reagent is an antibody or a lectin. In other embodiments, the reagent is conjugated to a fluorochrome or to magnetic particles. In particular embodiments, the cell selection is performed by a method comprising flow cytometry, fluorescence activated cell sorting, panning, affinity column separation, or magnetic selection.

In certain embodiments, the methods further comprise the steps of (d) introducing at least one selected cell to a culture medium that supports the growth of tumor stem cells; and (e) proliferating the selected cell in the culture medium. In other embodiments, the methods further comprise the step of: (f) introducing the proliferated cell into a host mammal. In some embodiments, the methods further comprise the steps of: (f) contacting the proliferated cell with a test compound; and (g) determining the effect of the test compound on the proliferated cell.

In certain embodiments, the present invention provides methods for stimulating an immune response to a solid tumor stem cell, comprising the steps of (a) obtaining an enriched population of solid tumor stem cells; wherein (i) the tumor cells are derived from a solid tumor; (ii) the solid tumor stem cell expresses ALDH1; (iii) the solid tumor stem cell is tumorogenic; and (iv) the solid tumor stem cell population is enriched at least 2-fold (e.g., 3-fold, 5-fold, 10-fold, 20-fold, etc.) relative to unfractionated tumor cells; (b) treating the population to prevent cell replication; and (c) administering the treated cell to a human or animal subject in an amount effective for inducing an immune response to solid tumor stem cells. In additional embodiments, the treatment kills the solid tumor stem cell. In some embodiments, the administration is by injection or by oral administration. In certain embodiments, the methods further comprise the step of (d) obtaining antibodies or antibody secreting hybridomas from the human or animal subject. In other embodiments, the methods further comprise the step of (e) testing the obtained antibody for the ability to specifically bind to solid tumor stem cells.

In some embodiments, the present invention provides methods for determining the effect of a test compound on a solid tumor stem cell, comprising the steps of: (a) obtaining an enriched population of solid tumor stem cells, wherein; (i) the tumor cells are derived from a solid tumor; (ii) the solid tumor stem cell expresses ALDH1; (iii) the solid tumor stem cells are tumorogenic; and (iv) the solid tumor stem cell population is enriched (e.g., 2-fold) relative to unfractionated tumor cells; (b) contacting the obtained cells with the test compound; and (c) determining the response of the contacted cells to the test compound.

In certain embodiments, the present invention provides methods for the proliferation of a tumor stem cells, comprising the steps of: (a) obtaining an enriched population of solid tumor stem cells, wherein; (i) the tumor cells are derived from a solid tumor; (ii) the solid tumor stem cell express ALDH1; (iv) the solid tumor stem cell is tumorogenic; and (iv) the solid tumor stem cell population is enriched (e.g., 2-fold) relative to unfractionated tumor cells; and (b) proliferating the obtained cells in a culture medium.

In other embodiments, the present invention provides methods for the proliferation of a tumor stem cells, comprising the steps of: (a) obtaining an enriched population of solid tumor stem cells, wherein; (i) the tumor cells are derived from a solid tumor; (ii) the solid tumor stem cell express ALDH1; (iii) the solid tumor stem cell is tumorogenic; and (iv) the solid tumor stem cell population is enriched at least (e.g., at least 2-fold) relative to unfractionated tumor cells; and (b) transplanting the isolated cell into a host mammal under conditions that allow the proliferation of solid tumor stem cells in the host mammal.

Examples of solid tumors from which solid tumor stem cells can be isolated or enriched for according to the invention include, but are not limited to, sarcomas and carcinomas such as, but not limited to: fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilms' tumor, cervical cancer, testicular tumor, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, meningioma, melanoma, neuroblastoma, and retinoblastoma.

DESCRIPTION OF THE FIGURES

FIG. 2A shows ALDH+ cells sorted from fresh reduction mammoplasties generate mammospheres in suspension culture, whereas ALDH-cells do not. FIG. 2B shows ALDH+ cells isolated from fresh tissue have a broader differential potential (progenies are CD10+ESA−, ESA+CD10+, CD10−ESA− and ESA+CD10−) compared to ALDH-cells which are predominantly ESA+). FIG. 2C shows that the ALDH+ population are enriched in progenitors cells which generate bi-potent progenies, whereas FIG. 2D shows that the ALDH− population presents only luminal epithelial cells.

FIG. 3A shows identification of the ALDH+ population in cells derived from a human breast tumor orthotopically xenotrans-planted in NOD/scid mice. ALDH activity was identified by flow cytometry, which shows enzymatically active cells retaining the fluorescent substrate in the right panel (A2). This population is absent when inhibitor of the enzyme is added (left panel, A1). FIG. 3B shows tumor progression and latency of tumor formation correlate with the number of unsorted cancer cells or ALDH+ cells injected. FIGS. 3B and 3C show that ALDH− cells are not tumorigenic.

FIG. 4A shows immunostaining of the ALDH−(A1, left) and ALDH+ (A2, right) populations detected by Aldefluor and separated by FACS. Percentage of the positive populations detected by the ALDH 1 antibody are shown on the M1 gate. FIG. 4B shows ALDH1 staining on paraffin embedded normal breast epithelium. FIG. 4C shows immunostaining of normal breast epithelium with cytokeratin 18 (Rhodamine-red) and ALDH1 (FITC-green), nuclei are stained blue with DAPI. FIG. 4D shows sections through paraffin embedded mammospheres, immunostained for ALDH1 (horseradish peroxidase-AEC-red). FIG. 4E shows immunostaining of mammospheres sections with cytokeratin 5 (FITC-green) and ALDH1 (Rhodamine-red). Nuclei are stained with DAPI.

FIG. 5D shows a Kaplan-Meyer analysis of the overall survival according to the ALDH1 status. ALDH1 positive tumors were associated with a poor prognosis. The difference in survival is statistically significant (p=0.045).

FIG. 7 *a-b* show representative flow cytometry analysis of ALDH activity in SUM-149 inflammatory breast carcinoma cells. Cells were incubated with ALDEFLUOR substrate (BAAA) and the specific inhibitor of ALDH, DEAB, was used to establish the baseline fluorescence of these cells (R1) and to define the ALDEFLUOR-positive region (R2) (a). Incubation of cells with ALDEFLUOR substrate in the absence of DEAB induces a shift in BAAA fluorescence defining the ALDE-FLUOR-positive population which represents 5.96±2.2% of the total population (b). All of the ALDEFLUOR analyses on human breast tumor cells were first gated on PI negative cells (viable cells) which represented 99.98±0.0282% (Mean±SDEV, n=7) of the total population. FIG. 7 *c-g* show only the ALDEFLUOR-positive population was tumorigenic. FIG. 7*c* shows the ALDEFLUOR-positive population was capable of regenerating the phenotypic heterogeneity of the initial tumor after passage in NOD/scid mice. FIG. 7*d* shows varying numbers of ALDEFLOUR-positive and ALDEF-LOUR-negative cells were injected in tumor growth was measured over a 75 day interval. No tumor was detected when 50,000 ALDEFLOUR-negative cells were injected. Whereas ALDEFLOUR-positive cells produced tumors which grew at a rate which directly correlated with the number of ALDF-LOUR-positive cells injected. FIG. 7*e* shows representative tumor grown in NOD/scid mice resulting from 50,000 ALDEFLUOR-positive cells and no tumor was detected when 50,000 ALDEFLUOR-negative cells were injected. Figure f-g show H & E staining demonstrating absence of tumor at the ALDEFLUOR-negative injection site). FIG. 7*h* shows that an invasion Matrigel assay showed that ALDE-FLUOR-positive cells invaded through Matrigel three-fold higher than ALDEFLUOR-negative cells. Figure i-n show only the ALDEFLUOR positive population displayed metastatic potential. FIG. 7 *i,l* show quantification of the normalized photon flux measured at weekly intervals following inoculations of 50,000 and 100,000 luciferase infected cells from each group (ALDEFLUOR-positive, ALDEFLUORnegative, unseparated). FIG. 7*j-k, m-n* show detection of metastasis utilizing the bioluminescence imaging software. Mice injected with 50,000 or 100,000 ALDEFLUOR-positive cells but not ALDEFLUOR-negative cells develop systemic metastasis. FIG. 7 *o-p* show histologic confirmation, on H&E sections, of metastasis in bone and lung resulting from injection of ALDEFLUOR-positive cells (arrows).

FIG. 8 *a-d* show an example of ALDH1 expression in a subset of cells in two different IBC samples. FIG. 8 *cd* show tumor emboli in dermal lymphatic demonstrate cells expressing ALDH1. FIG. 8 *e-f* show Kaplan-Meier survival curves according to ALDH1 status. ALDH1 expression is associated with decreased SS and MFS. FIG. 8*g-h* show Cox multivariate analysis after stepwise selection: ALDH1 was the strongest prognostic factor in SS and the only prognostic factor in MFS.

DEFINITIONS

Figure 1:
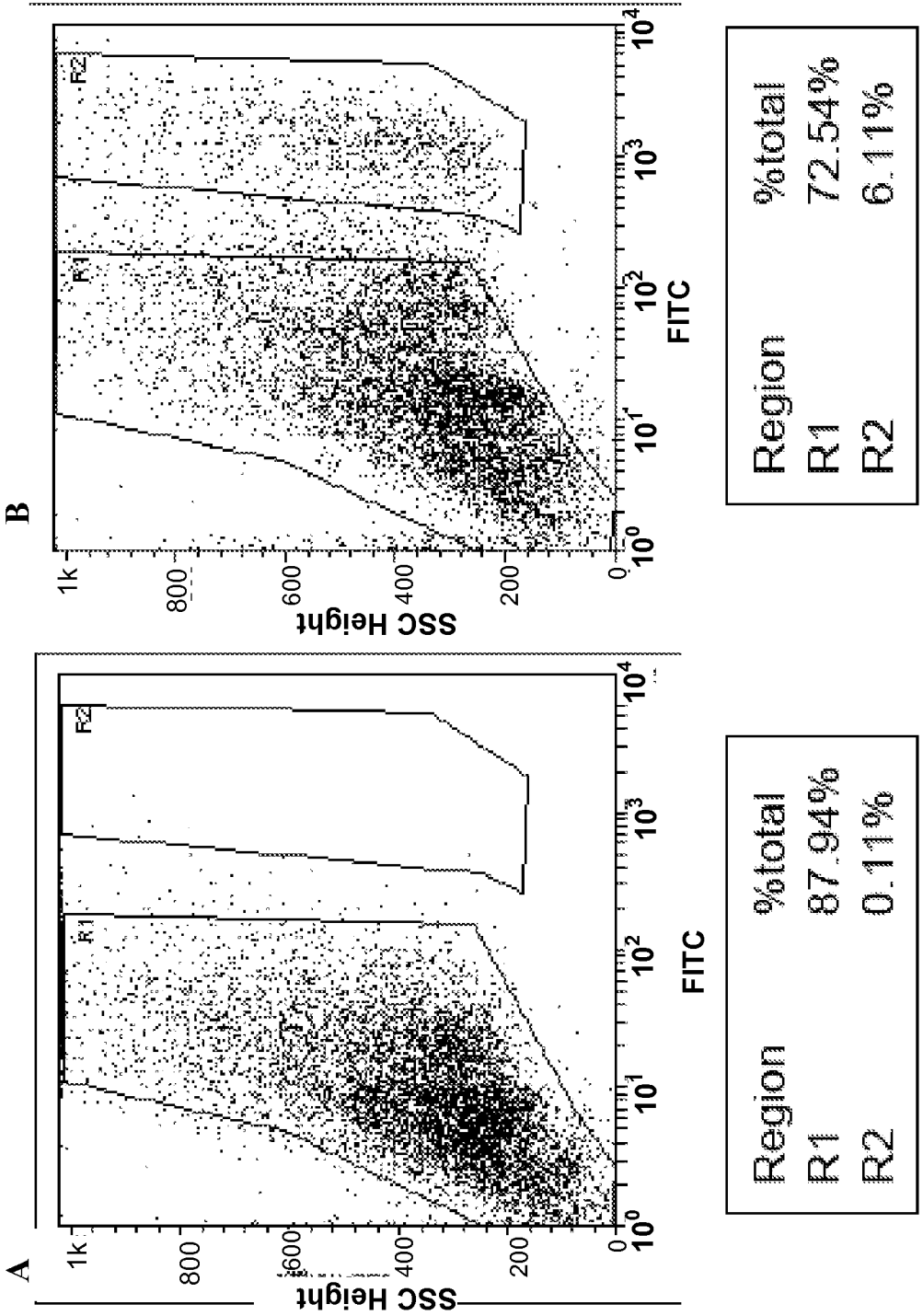
FIG. 1 shows identification of an ALDH positive population in the normal human breast epithelium by flow cytometry using the ALDEFLUOR kit. The left panel (A) represents the sample that was treated with the enzyme inhibitor, DEAB, the right panel (B) is the test sample. The R4 region represents the ALDH-population, the R6 the ALDH high population. The cells were gated on viability and side scatter. This sample is a representative example for the normal breast epithelial samples analyzed.

To facilitate an understanding of the present invention, a number of terms and phrases are defined below:

As used here, the term "antibody" includes monoclonal antibodies (including full length monoclonal antibodies), polyclonal antibodies, multispecific antibodies (e.g., bispecific antibodies), and antibody fragments so long as they exhibit the desired biological activity (e.g. able to bind a stem cell cancer marker as described herein). Antibodies can be conjugated to other molecules (e.g., toxins).

As used herein, the term "antibody fragments" refers to a portion of an intact antibody. Examples of antibody fragments include, but are not limited to, linear antibodies; single-chain antibody molecules; Fc or Fc' peptides, Fab and Fab fragments, and multispecific antibodies formed from antibody fragments.

As used herein, "humanized" forms of non-human (e.g., murine) antibodies are chimeric antibodies that contain minimal sequence, or no sequence, derived from non-human immunoglobulin. For the most part, humanized antibodies are human immunoglobulins (recipient antibody) in which residues from a hypervariable region of the recipient are replaced by residues from a hypervariable region of a non-human species (donor antibody) such as mouse, rat, rabbit or nonhuman primate having the desired specificity, affinity, and capacity. In some instances, Fv framework region (FR) residues of the human immunoglobulin are replaced by corresponding non-human residues. Furthermore, humanized antibodies can comprise residues that are not found in the recipient antibody or in the donor antibody. These modifications are generally made to further refine antibody performance. In general, the humanized antibody will comprise substantially all of at least one, and typically two, variable domains, in which all or substantially all of the hypervariable loops correspond to those of a nonhuman immunoglobulin and all or substantially all of the FR residues are those of a human immunoglobulin sequence. The humanized antibody can also comprise at least a portion of an immunoglobulin constant region (Fc), typically that of a human immunoglobulin. Examples of methods used to generate humanized antibodies are described in U.S. Pat. No. 5,225,539 to Winter et al. (herein incorporated by reference).

"Enriched," as in an enriched population of cells, can be defined phenotypically based upon the increased number of cells having a particular marker in a fractionated set of cells as compared with the number of cells having the marker in the unfractionated set of cells. However, the term "enriched" can be defined functionally by tumorigenic function as the minimum number of cells that form tumors at limit dilution frequency in test mice. For example, if 500 tumor stem cells form tumors in 63% of test animals, but 5000 unfractionated tumor cells are required to form tumors in 63% of test animals, then the solid tumor stem cell population is 10-fold enriched for tumorigenic activity. The stem cell cancer markers of the present invention can be used to generate enriched populations of cancer stem cells. In some embodiments, the stem cell population (e.g., based on the presence of ALDH1) is enriched at least 1.4 fold relative to unfractioned tumor cells (e.g. 1.4 fold, 1.5 fold, 2 fold, 5 fold, 10 fold, . . . , 20 fold, . . . ).

"Isolated" in regard to cells, refers to a cell that is removed from its natural environment (such as in a solid tumor) and that is isolated or separated, and is at least about 30%, 50%, 75%, 90% free, from other cells with which it is naturally present, but which lack the marker based on which the cells were isolated. The stem cell cancer markers of the present invention can be used to generate isolated populations of cancer stem cells.

As used herein, the terms "low levels," "decreased levels," "low expression," "reduced expression" or "decreased expression" in regards to gene expression are used herein interchangeably to refer to expression of a gene in a cell or population of cells, particularly a cancer stem cell or population of cancer stem cells, at levels less than the expression of that gene in a second cell or population of cells, for example normal breast epithelial cells. "Low levels" of gene expression refers to expression of a gene in a cancer stem cell or population of cancer stem cells at levels: 1) half that or below expression levels of the same gene in normal breast epithelial cells and 2) at the lower limit of detection using conventional techniques. "Low levels" of gene expression can be determined by detecting decreased to nearly undetectable amounts of a polynucleotide (mRNA, cDNA, etc.) in cancer stem cells compared to normal breast epithelium by, for example, quantitative RT-PCR or microarray analysis. Alternatively "low levels" of gene expression can be determined by detecting decreased to nearly undetectable amounts of a protein in cancer stem cells compared to normal breast epithelium by, for example, ELISA, Western blot, quantitative immunfluorescence, etc.

The terms "high levels", "increased levels", "high expression", "increased expression" or "elevated levels" in regards to gene expression are used herein interchangeably to refer to expression of a gene in a cell or population of cells, particularly a cancer stem cell or population of cancer stem cells, at levels higher than the expression of that gene in a second cell or population of cells, for example normal breast epithelial cells. "Elevated levels" of gene expression refers to expression of a gene in a cancer stem cell or population of cancer stem cells at levels twice that or more of expression levels of the same gene in normal breast epithelial cells. "Elevated levels" of gene expression can be determined by detecting increased amounts of a polynucleotide (mRNA, cDNA, etc.) in cancer stem cells compared to normal breast epithelium by, for example, quantitative RT-PCR or microarray analysis. Alternatively "elevated levels" of gene expression can be determined by detecting increased amounts of a protein in cancer stem cells compared to normal breast epithelium by, for example, ELISA, Western blot, quantitative immunfluorescence, etc.

The term "undetectable levels" or "loss of expression" in regards to gene expression as used herein refers to expression of a gene in a cell or population of cells, particularly a cancer stem cell or population of cancer stem cells, at levels that cannot be distinguished from background using conventional techniques such that no expression is identified. "Undetectable levels" of gene expression can be determined by the inability to detect levels of a polynucleotide (mRNA, cDNA, etc.) in cancer stem cells above background by, for example, quantitative RT-PCR or microarray analysis. Alternatively "undetectable levels" of gene expression can be determined by the inability to detect levels of a protein in cancer stem cells above background by, for example, ELISA, Western blot, immunofluorescence, etc.

As used herein, the term "receptor binding domain" refers to any native ligand for a receptor, including cell adhesion molecules, or any region or derivative of such native ligand retaining at least a qualitative receptor binding ability of a corresponding native ligand.

As used herein, the terms "cancer" and "cancerous" refer to or describe the physiological condition in mammals in which a population of cells are characterized by unregulated cell growth. Examples of cancer include, but are not limited to, carcinoma, lymphoma, blastoma, sarcoma, and leukemia. More particular examples of such cancers include squamous cell cancer, small-cell lung cancer, non-small cell lung cancer, adenocarcinoma of the lung, squamous carcinoma of the lung, cancer of the peritoneum, hepatocellular cancer, gastrointestinal cancer, pancreatic cancer, glioblastoma, cervical cancer, ovarian cancer, liver cancer, bladder cancer, hepatoma, breast cancer, colon cancer, colorectal cancer, endometrial or uterine carcinoma, salivary gland carcinoma, kidney cancer, liver cancer, prostate cancer, vulval cancer, thyroid cancer, hepatic carcinoma and various types of head and neck cancer.

"Metastasis" as used herein refers to the process by which a cancer spreads or transfers from the site of origin to other regions of the body with the development of a similar cancerous lesion at the new location. A "metastatic" or "metastasizing" cell is one that loses adhesive contacts with neighboring cells and migrates via the bloodstream or lymph from the primary site of disease to invade neighboring body structures.

The term "epitope" as used herein refers to that portion of an antigen that makes contact with a particular antibody.

When a protein or fragment of a protein is used to immunize a host animal, numerous regions of the protein can induce the production of antibodies which bind specifically to a given region or three-dimensional structure on the protein; these regions or structures are referred to as "antigenic determinants". An antigenic determinant can compete with the intact antigen (i.e., the "immunogen" used to elicit the immune response) for binding to an antibody.

The terms "specific binding" or "specifically binding" when used in reference to the interaction of an antibody and a protein or peptide means that the interaction is dependent upon the presence of a particular structure (i.e., the antigenic determinant or epitope) on the protein; in other words the antibody is recognizing and binding to a specific protein structure rather than to proteins in general. For example, if an antibody is specific for epitope "A," the presence of a protein containing epitope A (or free, unlabelled A) in a reaction containing labeled "A" and the antibody will reduce the amount of labeled A bound to the antibody.

As used herein, the terms "non-specific binding" and "background binding" when used in reference to the interaction of an antibody and a protein or peptide refer to an interaction that is not dependent on the presence of a particular structure (i.e., the antibody is binding to proteins in general rather that a particular structure such as an epitope).

As used herein, the term "subject" refers to any animal (e.g., a mammal), including, but not limited to, humans, non-human primates, rodents, and the like, which is to be the recipient of a particular treatment. Typically, the terms "subject" and "patient" are used interchangeably herein in reference to a human subject.

As used herein, the term "subject suspected of having cancer" refers to a subject that presents one or more symptoms indicative of a cancer (e.g., a noticeable lump or mass) or is being screened for a cancer (e.g., during a routine physical). A subject suspected of having cancer can also have one or more risk factors. A subject suspected of having cancer has generally not been tested for cancer. However, a "subject suspected of having cancer" encompasses an individual who has received an initial diagnosis but for whom the stage of cancer is not known. The term further includes people who once had cancer (e.g., an individual in remission).

As used herein, the term "subject at risk for cancer" refers to a subject with one or more risk factors for developing a specific cancer. Risk factors include, but are not limited to, gender, age, genetic predisposition, environmental exposure, previous incidents of cancer, preexisting non-cancer diseases, and lifestyle.

As used herein, the term "characterizing cancer in subject" refers to the identification of one or more properties of a cancer sample in a subject, including but not limited to, the presence of benign, pre-cancerous or cancerous tissue, the stage of the cancer, and the subject's prognosis. Cancers can be characterized by the identification of the expression of one or more cancer marker genes, including but not limited to, the cancer markers disclosed herein.

The terms "cancer stem cell," "tumor stem cell," or "solid tumor stem cell" are used interchangeably herein and refer to a population of cells from a solid tumor that: (1) have extensive proliferative capacity; (2) are capable of asymmetric cell division to generate one or more kinds of differentiated progeny with reduced proliferative or developmental potential; and (3) are capable of symmetric cell divisions for self-renewal or self-maintenance. These properties of "cancer stem cells," "tumor stem cells" or "solid tumor stem cells" confer on those cancer stem cells the ability to form palpable tumors upon serial transplantation into an immunocompromised mouse compared to the majority of tumor cells that fail to form tumors. Cancer stem cells undergo self-renewal versus differentiation in a chaotic manner to form tumors with abnormal cell types that can change over time as mutations occur. The solid tumor stem cells of the present invention differ from the "cancer stem line" provided by U.S. Pat. No. 6,004,528. In that patent, the "cancer stem line" is defined as a slow growing progenitor cell type that itself has few mutations but which undergoes symmetric rather than asymmetric cell divisions as a result of tumorigenic changes that occur in the cell's environment. This "cancer stem line" hypothesis thus proposes that highly mutated, rapidly proliferating tumor cells arise largely as a result of an abnormal environment, which causes relatively normal stem cells to accumulate and then undergo mutations that cause them to become tumor cells. U.S. Pat. No. 6,004,528 proposes that such a model can be used to enhance the diagnosis of cancer. The solid tumor stem cell model is fundamentally different than the "cancer stem line" model and as a result exhibits utilities not offered by the "cancer stem line" model. First, solid tumor stem cells are not "mutationally spared". The "mutationally spared cancer stem line" described by U.S. Pat. No. 6,004,528 can be considered a pre-cancerous lesion, while the solid tumor stem cells described by this invention are cancer cells that themselves contain the mutations that are responsible for tumorigenesis. That is, the solid tumor stem cells ("cancer stem cells") of the invention would be included among the highly mutated cells that are distinguished from the "cancer stem line" in U.S. Pat. No. 6,004,528. Second, the genetic mutations that lead to cancer can be largely intrinsic within the solid tumor stem cells as well as being environmental. The solid tumor stem cell model predicts that isolated solid tumor stem cells can give rise to additional tumors upon transplantation (thus explaining metastasis) while the "cancer stem line" model would predict that transplanted "cancer stem line" cells would not be able to give rise to a new tumor, since it was their abnormal environment that was tumorigenic. Indeed, the ability to transplant dissociated, and phenotypically isolated human solid tumor stem cells to mice (into an environment that is very different from the normal tumor environment), where they still form new tumors, distinguishes the present invention from the "cancer stem line" model. Third, solid tumor stem cells likely divide both symmetrically and asymmetrically, such that symmetric cell division is not an obligate property. Fourth, solid tumor stem cells can divide rapidly or slowly, depending on many variables, such that a slow proliferation rate is not a defining characteristic.

As used herein "tumorigenic" refers to the functional features of a solid tumor stem cell including the properties of self-renewal (giving rise to additional tumorigenic cancer stem cells) and proliferation to generate all other tumor cells (giving rise to differentiated and thus non-tumorigenic tumor cells) that allow solid tumor stem cells to form a tumor.

As used herein, the terms "stem cell cancer marker(s)," "cancer stem cell marker(s)," "tumor stem cell marker(s)," or "solid tumor stem cell marker(s)" refer to a gene or genes or a protein, polypeptide, or peptide expressed by the gene or genes whose expression level, alone or in combination with other genes, is correlated with the presence of tumorigenic cancer cells compared to non-tumorigenic cells. The correlation can relate to either an increased or decreased expression of the gene (e.g. increased or decreased levels of mRNA or the peptide encoded by the gene).

As used herein, the term "a reagent that specifically detects expression levels" refers to reagents used to detect the expression of one or more genes (e.g., including but not limited to, the cancer markers of the present invention). Examples of suitable reagents include but are not limited to, nucleic acid probes capable of specifically hybridizing to the gene of interest, aptamers, PCR primers capable of specifically amplifying the gene of interest, and antibodies capable of specifically binding to proteins expressed by the gene of interest. Other non-limiting examples can be found in the description and examples below.

As used herein, "providing a diagnosis" or "diagnostic information" refers to any information that is useful in determining whether a patient has a disease or condition and/or in classifying the disease or condition into a phenotypic category or any category having significance with regards to the prognosis of or likely response to treatment (either treatment in general or any particular treatment) of the disease or condition. Similarly, diagnosis refers to providing any type of diagnostic information, including, but not limited to, whether a subject is likely to have a condition (such as a tumor), information related to the nature or classification of a tumor, information related to prognosis and/or information useful in selecting an appropriate treatment. Selection of treatment can include the choice of a particular chemotherapeutic agent or other treatment modality such as surgery, radiation, etc., a choice about whether to withhold or deliver therapy, etc.

As used herein, the terms "providing a prognosis", "prognostic information", or "predictive information" refer to providing information regarding the impact of the presence of cancer (e.g.; as determined by the diagnostic methods of the present invention) on a subject's future health (e.g., expected morbidity or mortality, the likelihood of getting cancer, and the risk of metastasis).

The term "low risk" in regards to tumors or to patients diagnosed with cancer refers to a tumor or patient with a lower probability of metastasis and/or lower probability of causing death or dying within about five years of first diagnosis than all the tumors or patients within a given population.

The term "high risk" or "poor prognosis" in regards to tumors or to patients diagnosed with cancer refers to a tumor or patient with a higher probability of metastasis and/or higher probability of causing death or dying within about five years of first diagnosis than all the tumors or patients within a given population.

As used herein, the term "post surgical tumor tissue" refers to cancerous tissue (e.g., biopsy tissue) that has been removed from a subject (e.g., during surgery).

As used herein, the term "subject diagnosed with a cancer" refers to a subject who has been tested and found to have cancerous cells. The cancer can be diagnosed using any suitable method, including but not limited to, biopsy, x-ray, blood test, and the diagnostic methods of the present invention.

As used herein, the terms "biopsy tissue," "patient sample," "tumor sample," "biological sample," and "cancer sample" refer to a sample of cells, tissue or fluid that is removed from a subject for the purpose of determining if the sample contains cancerous tissue, including cancer stem cells. In some embodiment, biopsy tissue or fluid is obtained because a subject is suspected of having cancer. The biopsy tissue or fluid is then examined for the presence or absence of cancer, cancer stem cells, and/or cancer stem cell gene signature expression.

The term "siRNAs" refers to short interfering RNAs. In some embodiments, siRNAs comprise a duplex, or double-stranded region, of about 18-25 nucleotides long; often siRNAs contain from about two to four unpaired nucleotides at the 3' end of each strand. At least one strand of the duplex or double-stranded region of a siRNA is substantially homologous to or substantially complementary to a target RNA molecule. The strand complementary to a target RNA molecule is the "antisense strand;" the strand homologous to the target RNA molecule is the "sense strand," and is also complementary to the siRNA antisense strand. siRNAs can also contain additional sequences; non-limiting examples of such sequences include linking sequences, or loops, as well as stem and other folded structures. siRNAs appear to function as key intermediaries in triggering RNA interference in invertebrates and in vertebrates, and in triggering sequence-specific RNA degradation during posttranscriptional gene silencing in plants.

The term "RNA interference" or "RNAi" refers to the silencing or decreasing of gene expression by siRNAs. It is the process of sequence-specific, post-transcriptional gene silencing in animals and plants, initiated by siRNA that is homologous in its duplex region to the sequence of the silenced gene. The gene can be endogenous or exogenous to the organism, present integrated into a chromosome or present in a transfection vector that is not integrated into the genome. The expression of the gene is either completely or partially inhibited. RNAi can also be considered to inhibit the function of a target RNA; the function of the target RNA can be complete or partial.

The terms "overexpression" and "overexpressing" and grammatical equivalents, are used in reference to levels of mRNA to indicate a level of expression approximately 1.5-fold higher (or greater) than that observed in a given tissue in a control or non-transgenic animal. Levels of mRNA are measured using any of a number of techniques known to those skilled in the art including, but not limited to Northern blot analysis. Appropriate controls are included on the Northern blot to control for differences in the amount of RNA loaded from each tissue analyzed (e.g., the amount of 28S rRNA, an abundant RNA transcript present at essentially the same amount in all tissues, present in each sample can be used as a means of normalizing or standardizing the mRNA-specific signal observed on Northern blots). The amount of mRNA present in the band corresponding in size to the correctly spliced transgene RNA is quantified; other minor species of RNA which hybridize to the transgene probe are not considered in the quantification of the expression of the transgenic mRNA.

As used herein, the term "in vitro" refers to an artificial environment and to processes or reactions that occur within an artificial environment. In vitro environments can consist of, but are not limited to, test tubes and cell culture. The term "in vivo" refers to the natural environment (e.g., an animal or a cell) and to processes or reaction that occur within a natural environment.

The terms "test compound" and "candidate compound" refer to any chemical entity, pharmaceutical, drug, and the like that is a candidate for use to treat or prevent a disease, illness, sickness, or disorder of bodily function (e.g., cancer). Test compounds comprise both known and potential therapeutic compounds. A test compound can be determined to be therapeutic by screening using the screening methods of the present invention. In some embodiments of the present invention, test compounds include antisense compounds.

As used herein, the term "sample" includes a specimen or culture obtained from any source, as well as biological and environmental samples. Biological samples can be obtained from animals (including humans) and encompass fluids, solids, tissues, and gases. Biological samples include blood products, such as plasma, serum and the like. Environmental samples include environmental material such as surface matter, soil, water, crystals and industrial samples. Such examples are not however to be construed as limiting the sample types applicable to the present invention.

DESCRIPTION OF THE INVENTION

The cancer stem cells model has fundamental implications for cancer risk assessment, early detection, prognostication, and prevention. The current development of cancer therapeutics based on tumor regression may have produced agents which kill differentiated tumor cells while sparing the rare tumor stem cells population (see, e.g., Wicha et al., Cancer Research, 66:1883-1890, 2006 and Dontu et al., Stem Cell Reviews, 3(1):207-214, 2005, both of which are herein incorporated by reference). The development of more effective cancer therapies thus requires targeting this important cell population. The success of these new approaches is greatly benefited by the isolation and characterization of cancer stem cells from a many different histoclinical tumor subtypes.

The present invention indicates that ALDH is a marker of normal stem cells from the human breast and for cancer stem cells of breast carcinomas. In addition to oxidation of intracellular aldehydes, ALDH also confers resistance to alkylating agents, such as cyclosphamide (e.g., Sophos et al., Chem. Biol. Interact, 5(22):143-144, 2003). More than 17 human ALDH genes have been identified, and the ALDH superfamily is highly conserved across a variety of species. ALDH1 class comprises the cytosolic isoforms. It has been speculated that ALDH might have a role in the protection of the long lived primitive cells against oxidative agents. Stem and progenitor cells are known to have increased activity of defense mechanisms such as membrane transporters responsible for the efflux of damaging agents and increased DNA repair activity. Increased ALDH activity might contribute through its detoxification function, to the inherent resistance of stem cells to toxic insults. Moreover, ALDH is involved in the conversion of retinol into retinoic acid, an important player in cell differentiation, cell proliferation and cell survival (Duester et al., Eur J. Biochem., 267:4315-4324, 2000). It is possible therefore, that in addition to its role in detoxification, ALDH also functions in cell fate determination in stem and progenitor cells.

The present invention provides many advantages through the use of ALDH as a marker for stem cells. For example, many different types of cancer stem cells can be identified (e.g., breast cancer and colon cancer stem cells). Also, the techniques provided by the present invention for detecting and isolating the ALDH+ population in easy to use and have a high level of reproducibility, by contrast to the complex phenotypes defined by multiple surface markers. Unlike certain other functional assays, such as exclusion of dyes that bind to nucleic acids, methods of the present invention can be non-toxic for the cells.

Work conducted during the development of the present invention has shown that the ALDH positive cell population, representing 6% of the normal breast epithelial cells, has stem cell characteristics. Phenotypic markers associated with stem and progenitor cells segregated with the ALDH positive population. Also the mammosphere initiating cells, which according to previous studies are likely to be the normal breast stem cells are contained in the ALDH positive fraction of the mammary epithelium. Furthermore, the ALDH positive population contains the cancer stem cell population, as shown by the ability to generate tumors in mice. As few as 500 ALDH positive cells generate tumors upon implantation in NOD/scid mice, whereas the ALDH negative population is not tumorigenic, even when implanted in high numbers (50,000). The latency and size of the tumor correlated with the number of ALDH+ cell implanted.

Work conducted during the development of the present invention has shown that ALDH positive cells can be detected in situ by immunostaining with ALDH 1 antibody. There is considerable overlap between the ALDH positive population detected in situ by immunostaining and the ALDH positive population detected by the FACS-based enzymatic assay (see Examples below). As such, the present invention allows cancer stem cell detection methods in situ, such as in paraffin embedded sections, as part of the routine pathological exam.

The present invention is not limited to a particular mechanism. Indeed, an understanding of the mechanism is not necessary to practice the present invention. Nonetheless, it is contemplated that experiments conducted during the course of development of the present invention provide that ALDH1 expression in some tumors may reflect transformation of ALDH+ stem or early progenitor cells, rather than transformation of later, ALDH− progenitor cells, as may be the case in the ALDH− tumors. In the ALDH+ tumors, the cancer stem cell population inherits properties of normal stem cells that confer a higher aggressiveness (higher proliferation potential, resistance to damaging agents, therefore chemoresistance). The present invention is not limited to a particular mechanism. Indeed, an understanding of the mechanism is not necessary to practice the present invention. Nonetheless, it is contemplated that experiments conducted during the course of development of the present invention provide that the ALDH+ population might be above levels of detection on TMAs only in tumors with a larger percentage of the ALDH+ cells. The larger size of the ALDH+ population may be due to an increased self-renewal activity in these tumors. A recent study showed that a gene signature associated with increased self-renewal of normal cells is a predictor of poor prognosis (Glinsky et al., J. Clin. Invest., 115(6):1503-1521, 2005 and Lahad et al., J. Clin Invest. 115(6):1463-1467, 2005). Regardless of these interpretations, it is likely that the breast carcinomas that have a low percentage of ALDH+ cells could not be detected using microarrays in the Examples below due to the small number of cells in the three cores representing a sample on the TMAs (no more than 500-600 cells).

Work conducted during the development of the present invention has shown that the ALDH positive cell populations may be located in the terminal ductal lobular units (TDLUs). In particular, immunostaining of paraffin-embedded sections of normal breast epithelium using an ALDH1 antibody identified a relatively rare population of ALDH1-positive cells located in the terminal ductal lobular units. ALDH-1 positive cells appeared to form a bridge in the lumen that could be located at the bifurcation point of side branches in the TDLUs.

Work conducted during the development of the present invention has shown that ALDH1 protein expression is linked to clinical outcome. Analysis of overall survival (OS) showed a strong association of ALDH1-positive tumors with poor clinical outcome for two large populations of breast cancer cells. In a first set of 136 samples analyzed on tissue microarrays, the 5-year OS was 19.8% [14.52-97.28] for patients with an ALDH1-positive tumor and 58.7% [33.22-100] for patients with an ALDH1-negative tumor. In a second set of 345 samples analyzed on tissue microarray, the 5-year OS was 69.59% [60.73-79.73] for patients with an ALDH 1-positive tumor and 84.55% [80.02-89.33] for patients with an ALDH1-negative tumor. A Cox multivariate analysis was performed of OS in which the values for ALDH1, tumor size, age, lymph node metastasis, histological grade, ER, PR, Ki-67 and ERBB2 were considered as categorical variables. ALDH1 expression was an independent prognostic factor, as was Ki-67 status, tumor size, and histological grade. The relative risk of death due to cancer was 1.76 for patients with ALDH1-positive tumors compared to patients with ALDH1-negative tumors ($p<0.028$).

The present invention constitutes a major advance in the field since the cancer stem cell model for diagnostic and prognostic depend in a large measure on the ability to identify cancer stem cells in situ, which is made possible by the present invention.

The present invention is not limited by the type of cancer stem cell that can be detected. In certain embodiments, the cancer stem cells are breast cancer stem cells. In other embodiments, the cancer stem cells are colon cancer stem cells.

In certain embodiments, ALDH 1 is employed as a tumor biomarker for predicting multiple colorectal cancer (CRC) related clinical variables based on an assay for colonic stem cells. Such methods that may be employed include, but are not limited to: 1) assessment of CRC risk according to the number of colonic crypt stem cells in colonic epithelial samples; 2) early detection of colonic tumors (adenomas or CRC) based on an assay to detect colonic stem cells in stool or in blood samples; 3) personalized prediction of the efficacy of chemopreventive agents that are designed to control colonic stem cell number; 4) prognostic indicator to enumerate tumor stem cells in samples from colon tumors in patients diagnosed with CRC; 5) monitoring of therapeutic response based on the number of colonic stem cells in circulating blood or the number of tumor stem cells in tumor tissue samples from resected cancers following neoadjuvant therapy; 6) prediction of therapeutic response to systemic agents or radiotherapy based on the number or distribution of colonic stem cells in tumors or in circulating blood; and 7) an indicator for adjuvant treatment based on stem cell number in tumor samples or in circulating blood.

In other embodiments, ALDH1 is employed as a therapeutic target in colorectal cancer treatment. Such methods that may be employed include, but are not limited to: 1) drugs or agents that inhibit or stimulate ALDH1 enzyme activity in colonic epithelial cells, where the drugs may be used individually or in combination with other anti-cancer therapeutics; 2) drugs or agents that control, reduce or eliminate ALDH1 positive colonic cells, where the drugs may be used individually or in combination with other anti-cancer therapeutics; 3) molecular agents such as immunotherapeutics or anti-sense molecules that modulate ALDH1 levels in colonic epithelial cells; 4) molecular agents such as transcription factor modulators or microRNA-based molecules that modulate ALDH1 expression and consequently modulate ALDH1 levels in colonic epithelial cells; and any agents from above that modify the response to radiation therapy for patients with colon cancer. It is noted that all of the above diagnostic and therapeutics methods may also be used for other types of cancers as well.

Inflammatory Breast Cancer and ALDH1

Inflammatory breast cancer (IBC) is a highly angio-invasive form of breast cancer associated with a high incidence of early nodal and systemic metastasis. In spite of advances utilizing systemic chemotherapy, the prognosis of IBC remains poor compared to other locally-advanced breast cancers (LABC). Although several molecular changes including RHOC overexpression or deletion of the tumor suppressor WISP3 have been associated with IBC, there are currently no biologic prognostic or predictive markers which have been demonstrated to be predictive of metastasis or survival in these patients. This highlights the importance of understanding the factors which contribute to the metastatic character and resultant poor prognosis of IBC.

Utilizing in vitro and mouse models as described in Example 5 below, it has been demonstrated that invasion and metastasis in inflammatory carcinoma are mediated by a cellular subcomponent with cancer stem cell characteristics. In a series of 109 patients with inflammatory breast carcinoma, expression of the stem cell marker ALDH 1 was associated with early metastasis and decreased survival. The present invention demonstrates that the aggressive nature of inflammatory breast carcinoma is mediated by its cancer stem cell component.

Work conducted during the development of the present invention has demonstrated that ALDH-expressing IBC cells have properties of cancer stem cells, are highly invasive and are able to mediate metastasis in NOD/SCID mice. The present invention has also shown that the expression of the stem cell marker ALDH1 can predict metastasis and overall clinical outcome in patients with inflammatory breast carcinoma. These results indicate that cancer stem cells play an important role in mediating the clinically aggressive behavior of inflammatory breast carcinoma. Due to its highly aggressive metastatic behavior, this cancer is currently treated with an aggressive course of neoadjuvant chemotherapy. The use of the prognostic and predictive markers ALDH 1 will allow for more tailored treatment and novel therapeutic approaches (e.g., anti-ALDH 1 antibodies) to target this cell population resulting in improved clinical outcome in these patients.

BRCA1 and ALDH1 in Cancer Stem Cells

Worked conducted during the development of the present invention, utilizing both in vitro systems and a humanized NOD/SCID mouse model, demonstrated that BRCA1 expression is required for the differentiation of ER-negative stem/progenitor cells to ER-positive luminal cells. This work showed that knockdown of BRCA1 in primary breast epithelial cells leads to an increase in cells displaying the stem/progenitor cell marker ALDH1 and a decrease in cells expressing luminal epithelial markers and estrogen receptor. In breast tissues from women with germline BRCA1 mutations, but not normal controls, this work detected entire lobules which, although histologically normal, were positive for ALDH1 expression but negative for the expression of ER. Loss of heterozygosity (LOH) for BRCA1 was documented in these ALDH1-positive lobules but not in adjacent ALDH1-negative lobules. Taken together, this work demonstrates that BRCA1 plays a critical role in the differentiation of ER negative stem/progenitor cells to ER positive luminal cells. Since BRCA1 also plays a role in DNA repair, this work indicates that loss of BRCA1 may result in the accumulation of genetically unstable breast stem cells providing prime targets for further carcinogenic events.

EXPERIMENTAL

The following examples are provided in order to demonstrate and further illustrate certain some embodiments and aspects of the present invention and are not to be construed as limiting the scope thereof.

In the experimental disclosure which follows, the following abbreviations apply: N (normal); M (molar); mM (millimolar); µM (micromolar); mol (moles); mmol (millimoles); µmol (micromoles); nmol (nanomoles); pmol (picomoles); g (grams); mg (milligrams); µg (micrograms); ng (nanograms); l or L (liters); ml (milliliters); µl (microliters); cm (centimeters); mm (millimeters); µm (micrometers); nm (nanometers); and ° C. (degrees Centigrade).

Materials and Methods for Examples 1-4

Tumor Samples

Two metastatic breast cancers established as xenotransplants in NOD/scid animals were used, MCI a pleura effusion ER–PR–Her2, and an ovarian metastasis, UM2, ER+PR+ Her2–.

Animal Model:

NOD/scid mice were used to assess the tumorigenicity of the ALDH positive population, compared to the population and the unsorted population. The animal model was described by Kuperwasser et al. for xenotransplantation of normal mammary epithelial cells (Kuperwasser et al., PNAS, 101:4966-71, 2004, herein incorporated by reference). The fat pads were cleared pre-puberty and humanized by injecting a mixture of irradiated and non-irradiated immortalized human fibroblasts (1:1 irradiated:non-irradiated, 50,000 cells/100 µl Matrigel/fat pad). The immortalized fibroblasts were primary human mammary fibroblasts with retroviral transfected with a retrovirus construct expressing telomerase. Implantation of the human cancer cells, in a mixture with fibroblasts was done 2-4 weeks later. The cancer cells were obtained by mechanical and enzymatic dissociation of tumor. The animals were euthanized when the tumors are approximately 0.8 cm in the larger diameter, to avoid necrosis in the tumor.

Dissociation of Mammary Tissue

Normal breast tissue from reduction mammoplasties was minced with scalpels and dissociated enzymatically as previously described (Dontu et al., Gen. & Dev., 17(1):1253-1270, 2003, herein incorporated by reference).

Mammosphere Culture

Single cells were plated in ultra-low attachment plates (Corning) or plates coated with 1% agarose in PBS, at a density of 10,000 viable cells/ml in primary culture and 5000 cells/ml in subsequent passages. For mammosphere culture, cells were grown in a serum-free mammary epithelial basal medium (MEBM) (Cambrex Bio Science Walkersville, Inc, Walkerville, Md.) with supplements for 7-10 days as previously described.

Differentiating Culture Conditions

Single cell suspensions were plated on collagen-coated plates at a density of 2000 viable cells/10 cm diameter dish. Cells were grown in Ham's F-12 medium (BioWhittaker) with 5% fetal bovine serum (FBS), 5 µg/ml insulin, 1 µg/ml hydrocortisone, 10 µg/ml cholera toxin (Sigma), 10 ng/ml epidermal growth factor (BD Biosciences) and 1× Pen/Strep/Fungizone Mix (BioWhittaker).

Aldefluor Assay and Separation of the ALDH Positive Population by FACS

The Aldefluor kit was used for labeling the ALDH positive population, according to the manufacturer's protocol (StemCell Technologies). Briefly, the ALDEFLUOR assay works by providing cells with a substrate for ALDH, called BAAA, that fluoresceces when converted to BAA in the cells. BAA is retained intracellularly by the cells and then can be detected by green fluorescence (FL1) channel or standard flow cytometry. The sorting gates were established using as negative controls the DAPI or PI stained cells for viability, the ALDEFLUOR stained cells treated with inhibitor of the enzyme (DEAB), according to the manufacturer's protocol, and the staining with secondary antibody alone. The secondary antibody (labeled with PE) was used in combination with an anti-H2Kd antibody for staining and excluding H2Kd positive cells, of mouse origin, possibly contaminating the xeontransplanted tumors. The TMAs were provided by the Tissue Microarray Core laboratory at University of Michigan Medical School and by the laboratory of molecular oncology at the Institute de Cancerologie de Marseille, Inserm, FRANCE. Clinical and histopathological data were available for these patients.

Flow Cytometry

Cells were stained fresh or after fixation in methanol. Primary antibodies ESA, CD10 (dilution 1:25) (Novocastra) 31, DC140b and H2kd (Parmingen) dilutions 1:50, 1:20, 1:50 and 1:50 respectively, CD2, CD3, CD16, CD18 labeled with PE-Cy5 (Pharmingen,) dilution 1:30 and CD 10, CD 64 labeled with PE-Cy5 ((Pharmingen) at a dilution of 1:20 at the concentration recommended by the manufacturer. Incubation was performed for 30 min on ice temperature in Hanks Balanced Salt Solution (HBSS) with 2% FBS, followed by washing in HBSS with 2% FBS. The same procedure was followed for staining with secondary antibody, anti-goat IgG or antirabbit IgG, labeled with FITC (1:200 dilution; Jackson Labs), goat antimouse IgG1 and goat antimouse IgG2b, labeled with Tricolor (PE-Cy5), (Caltech laboratories) at final dilution 1:100. After incubation, cells were washed once with HBSS (BioWhittaker) and were resuspended in HBSS supplemented with 5% FBS. Cells were stained with 1 µg/ml propidium iodide (Sigma) for 5 min for viability. Analysis was performed using FACStarPLUS (Becton Dickinson, Palo Alto, Calif., USA) and the Elite SP (Becton Dickinson) flow cytometer.

Immunostaining

To assess the lineage composition of the colonies, cells were fixed on plates for 20 min in methanol, at −20° C., and were then stained using Peroxidase Histostain-Plus and Alkalinephosphatase Histostain-Plus kits (Zymed, South San Francisco, Calif., USA), according to the manufacturer's protocol. The paraffin embedded sections through mammospheres and normal breast tissue and the TMA were deparaffinized. Citrate pH=6.5 retrieval antigen was used for the ALDH1 staining. The primary antibodies—epithelial-specific antigen and cytokeratin 18 for epithelial cells, CD10 and cytokeratin 14, Cytokeratin 5 (Novocastra, Newcastle-upon-Tyne, UK) for myoepithelial cells—were used at the dilutions indicated by the manufacturer. ALDH1 antibody (BD Biosciences) was used at 1:50 dilution for IHC and 1:100 for FACS. AEC and DAB (Zymed) were used as substrates for peroxidase, and NBT/BCIP (Gibco/BRL, Gaithersburg, Md., USA) was used for alkaline phosphatase. FITC-labeled and Texas-red labeled secondary antibodies (Jackson Labs, West Grove, Pa., USA) were used for fluorescent microscopy. Nuclei were stained with DAPI.

Biostatistical Analysis

For establishing correlation with prognosis and other histoclinical parameters, the software R, version 2.3.0 was used.

Example 1

ALDH Positive Population Isolated from the Normal Mammary Epithelium Has Stem Cell Like Characteristics The ALDEFLUOR test was utilized to assess the presence and size of the ALDH+ population in normal human breast samples. Single cell suspensions of normal mammary epithelial cells were obtained by mechanical and enzymatic digestion of mammoplasty samples, as previously described (Dontu et al., supra). Analysis of samples from 8 different patients showed an average of 6% ALDH+ population, in normal mammary epithelial cells (FIG. 1).

Figure 2:
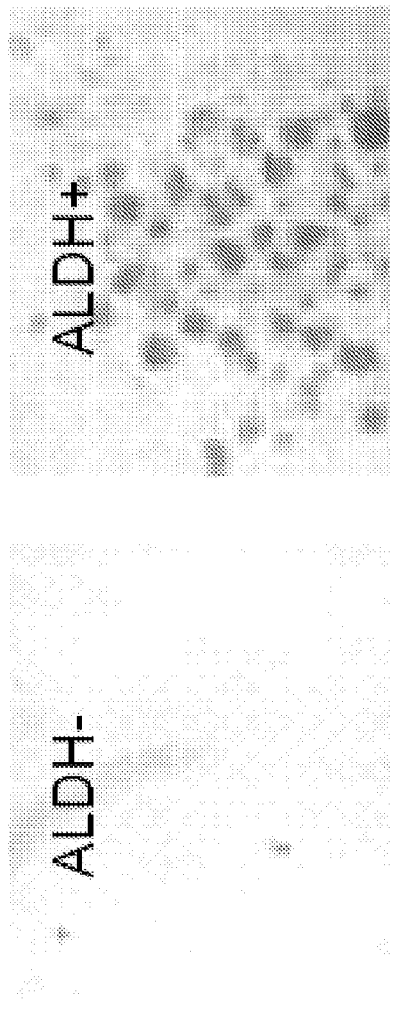
FIG. 2 shows ALDH+ cells isolated from the normal breast have stem-cell properties in in vitro assays.
Figure 2:
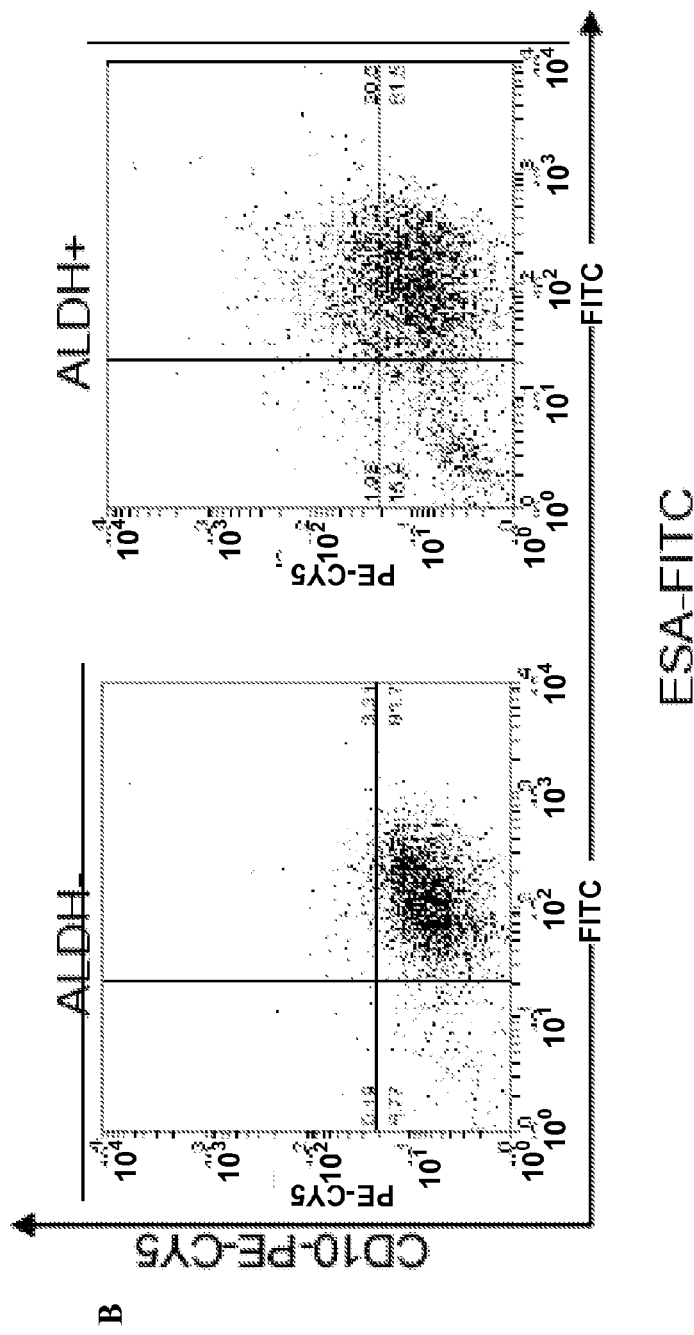
Figure 2:
Figure 2:
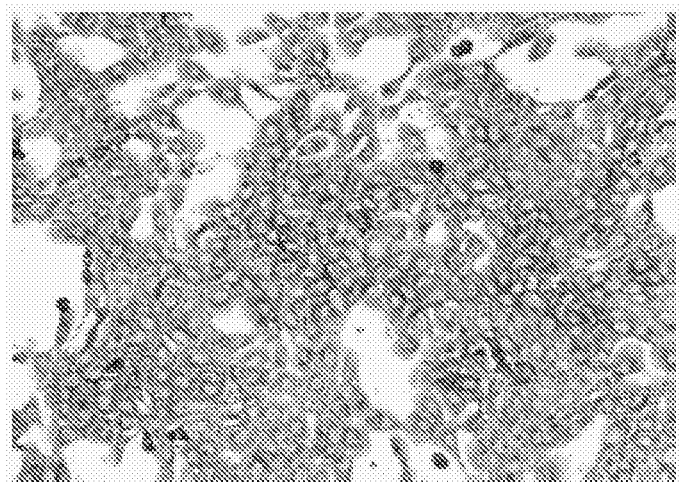

The clonegencity of this population was analyzed in suspension culture (non-adherent mammospheres) and on collagen substratum (conditions that promote differentiation). Only the ALDH positive population was capable of generating mammospheres in suspension culture, whereas the ALDH negative population failed to grow in anchorage independent conditions (FIG. 2 A). Previously published data supports the idea that the mammary epithelial cell population that survives in anchorage independent conditions, and proliferates to generate floating spherical colonies (mammospheres), is likely the stem cell population (Dontu et al., supra). A considerable higher clongenicity (10 fold) and proliferation potential was found in the ALDH+ population compared to the ALDH− population, in culture on collagen substratum. Moreover, the ALDH+ population was enriched in bi-potent progenitor cells, capable of differentiation along both myoepithelial and luminal epithelial lineages (the two major cell lineages present in the non-lactating mammary gland).

The differentiation potential of ALDH+ and ALDH− populations was tested by placing the sorted cells in culture on a collagen substratum in the presence of serum (differentiating conditions) for 12 days. In clonogenic assays, this was done at low cell density which allowed in situ staining and scoring of colonies generated by individual cells, in order to determine their differentiation potential. Markers specific for the myoepithelial lineage (CD10, cytokeratin 14) and luminal epithelial lineage (ESA, cytokeratin 18) were used for immunostaining. Bi-potent progenitor cells were enriched 4 fold in the ALDH+ population compared to the ALDH-population. Differentiation potential of ALDH+ and ALDH− populations was also tested by flow cytometry. The distribution of lineage markers in the entire population of progeny cells generated in differentiating conditions by these sorted populations was analyzed (FIG. 2B). The results were similar to the ones obtained in the clonogenic assay. The ALDH+ population was enriched in progenitors cells which generated bi-potent progenies (CD10−ESA−, CD10+ESA+), myoepithelial (CD10+) and luminal epithelial cells (ESA+) (FIG. 2B right panel). The ALDH-population contained progenitors restricted to the luminal epithelial cell fate (ESA+) (FIG. 2B, left panel) and the ALDH low population contained bi-potent progenitors and progenitors restricted to the myoepithelial fate (CD10+). The ALDH+ population was enriched in progenitors cells which generate bi-potent progenies (ESA+

CD10+) (FIG. 2C) whereas the ALDH− population presented only luminal epithelial cells (ESA+) (FIG. 2D).

Example 2

Figure 3:
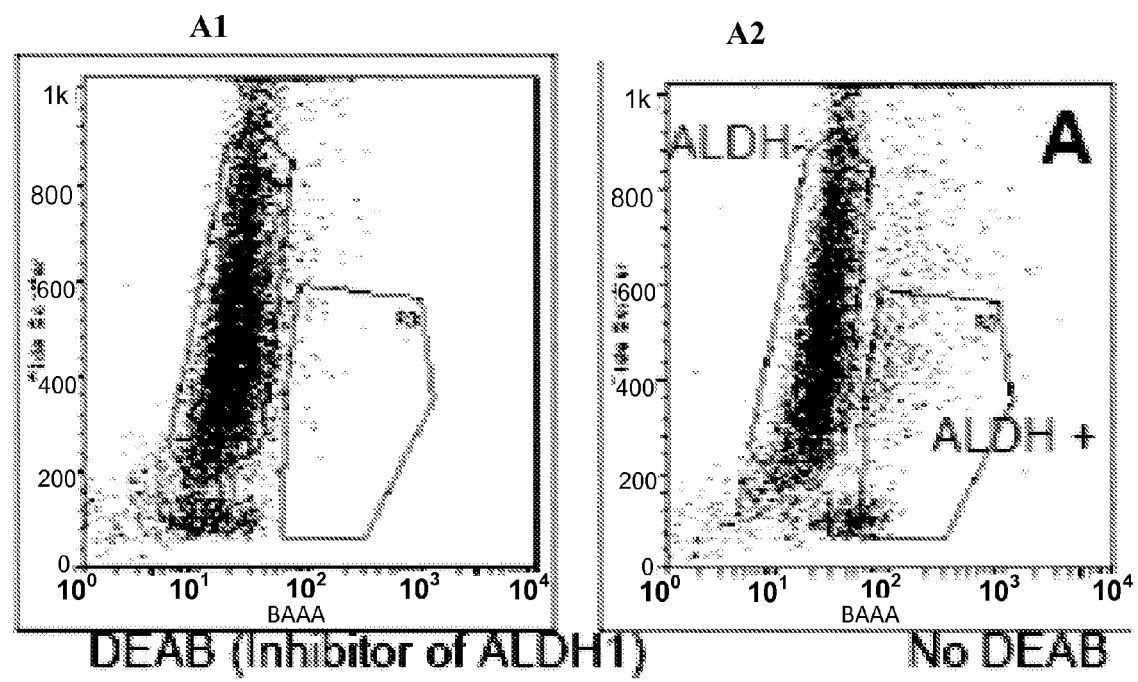
FIG. 3 shows tumorigenicity of the ALDH+ population in NOD/scid mice.
Figure 3:
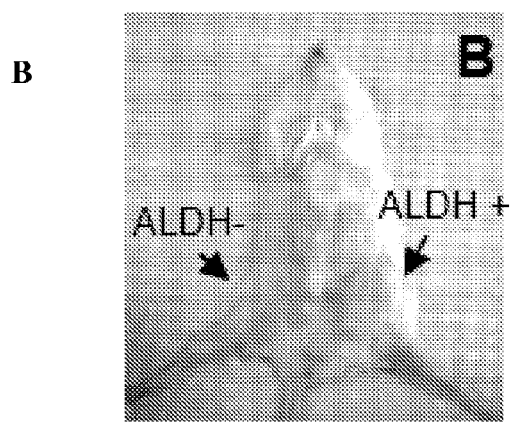
Figure 3:
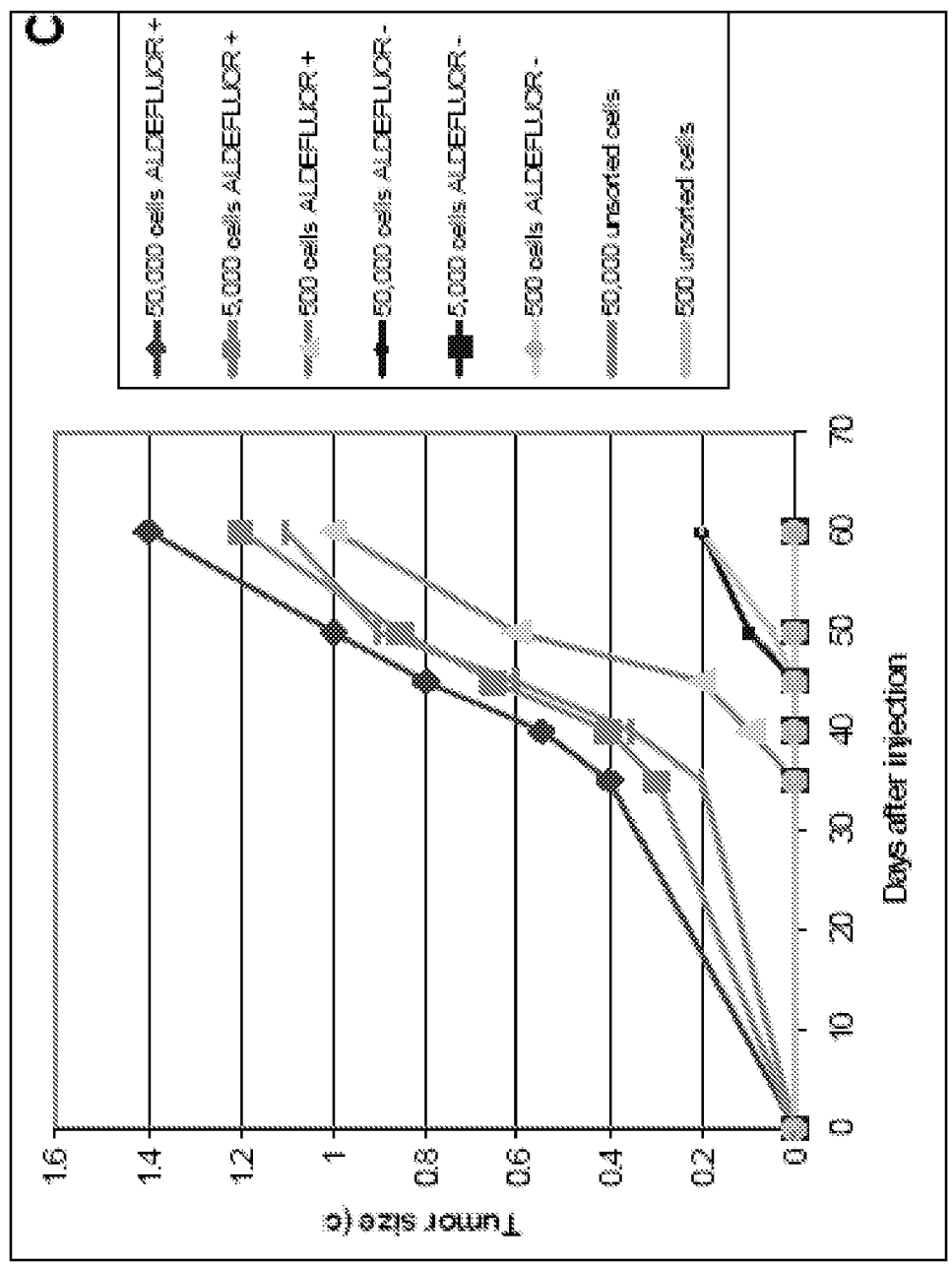

Tumorigenicity of the ALDH Positive Cells Isolated from Human Breast Cancers The same Adefluor test was used to investigate the representation of the ALDH+ population in breast cancer cells. Two human breast cancers (MCI an ER−PR−Her2-tumor and UM2, an ER+PR+Her2-tumor) were analyzed orthotopically xenotransplanted in NOD/scid mice (these cells were not grown in vitro). The ALDH+ population was present and represented approximately 5% (MCI) and 8% (UM2) of the total cell population. The tumorigenicity of the ALDH+ population sorted from MCI was tested in serial passages, using limiting dilutions of cells (50,000 cells, 5000 cells and 500 cells). Three passages were performed, and in all three only the ALDH+ cells formed tumors, even when implanted in low numbers. As shown in FIG. 3 C, size and latency of tumor formation correlated with the number of ALDH+ cells injected. Remarkably, ALDH+ cells were capable to generate a tumor in only a month, from 500 cells injected. ALDH− cells failed to grow tumors, even when implanted in high numbers. The growth in the fat pad implanted with 50,000 ALDH− cells is consistent with the existence of approx 0.1% contaminating ALDH+ cells, which is well within the limits of flow cytometry error. Moreover, the ALDH+ population regenerated the initial heterogeneity of the tumor, as shown by the presence of both ALDH+ and ALDH− populations in the passaged tumors grown from ALDH+ cells (data not shown). These characteristics indicate that the ALDH+ population contains the cancer stem cell population of this tumor. Similar results were obtained for the UM2 tumor.

The overlap between the CD44+CD24−lin−(CD2−CD3−CD10−,CD16−CD18−CD31−CD64−CD140b−) population and the ALDH+ population was analyzed and a small overlap was found. Eight percent (8%) of the CD44+CD24−lin− is ALDH+ and 12% of the ALDH+ populations is CD44+CD24−lin−. In all these experiments the mouse cells were eliminated, by staining with H2Kd antibody. DAPI or PI staining was used for viability.

Example 3

In Situ Immunostaining Using ALDH1 Antibody

The early studies showing a correlation between ALDH expression and hematopoietic stem cells used fixed cells and staining with ALDH1 antibody (Kastan et al., Blood, 75:1947-1950, 1990, herein incorporated by reference). ALDH being a cytosolic enzyme, this method is not useful for studies in which functional properties of the ALDH positive cells need to be assessed. The ALDEFLUOR kit was developed to address this problem. Viable cells that express ALDH 1 can be isolated by flow cytometry, using fluorescent aldehyde substrates that freely diffuse across cell membranes. Using this enzymatic assay and flow cytometry activated cell sorting (FACS), ALDH+ cells can be isolated and cultured or used in in vivo experiments.

However, the in situ detection of normal or cancer stem cells, is an important step forward for the application in of cancer stem concepts to clinical practice, by enabling the use of stem cell markers in roution exam on patient samples and archived tissues. The ALDH1 antibody (commerically available from BD Biosciences) identifies all the ALDH class 1 isoforms, which are responsible for the cytosolic enzymatic activity detected by the Aldefluor kit. The two assays should identify the same cellular population, although the ALDE-FLUOR kit kit might also detect additional cells with activity due to mitochondrial isoforms (class 2 ALDH) and microsomal isoforms (class 3 ALDH). Differences due to the sensitivity of the two methods are also expected. To determine if this is indeed the case, the overlap between the ALDH+ populations identified using the Aldefluor kit and the ALDH+ population identified by immunocytochemistry was assessed. The ALDH positive and negative populations from normal breast epithelium were isolated by FACS and stained with ALDH 1 antibody.

Figure 4:
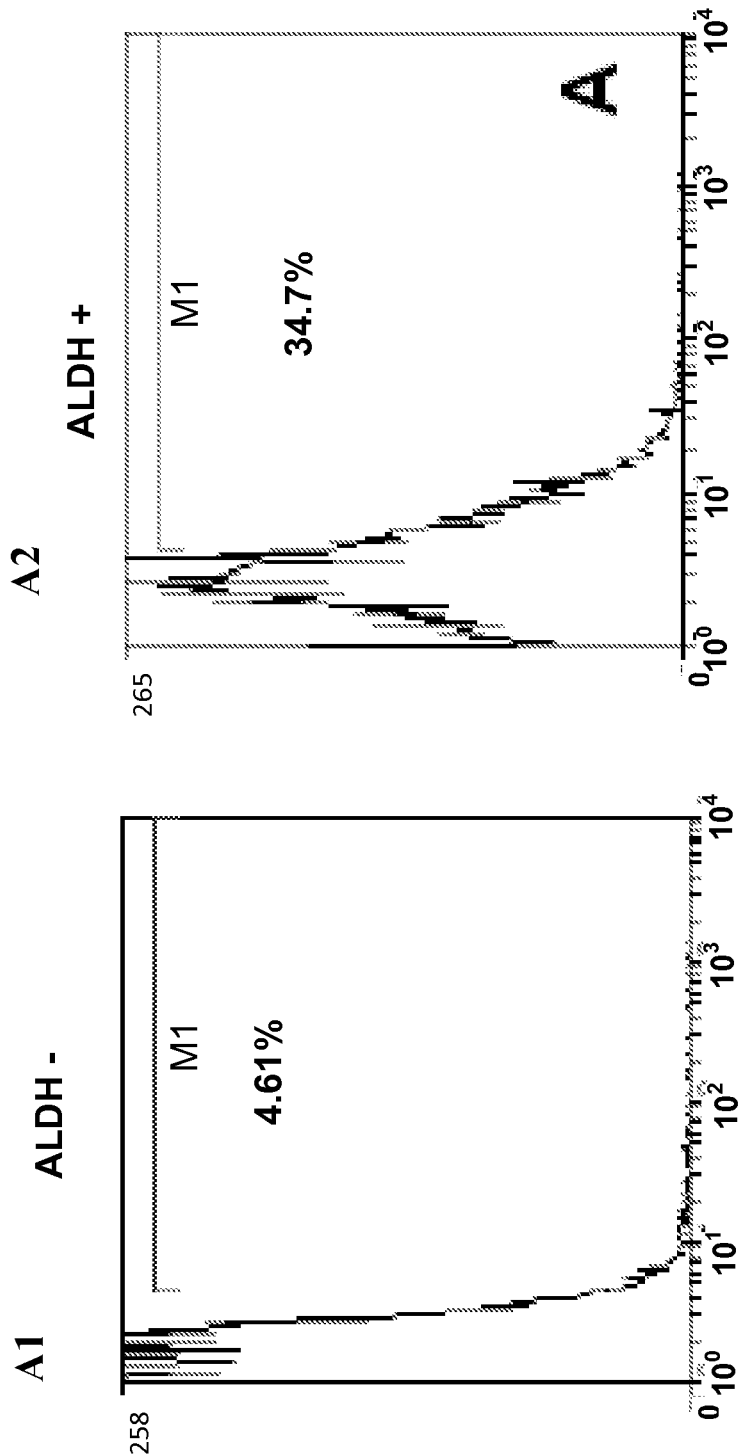
FIG. 4 shows in situ detection of ALDH1+ population.
Figure 4:
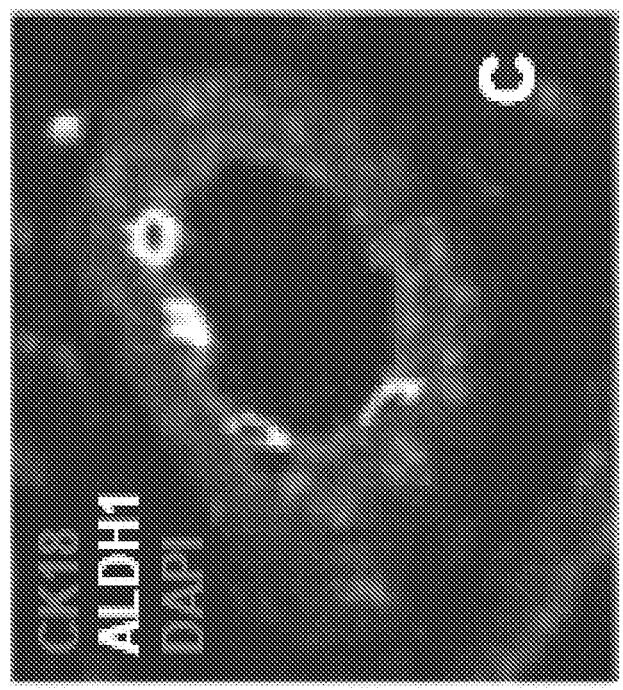
Figure 4:
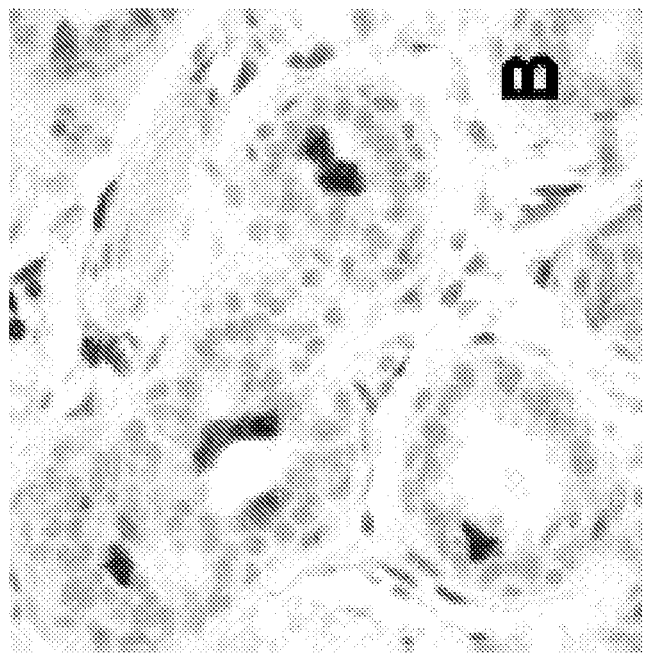
Figure 4:
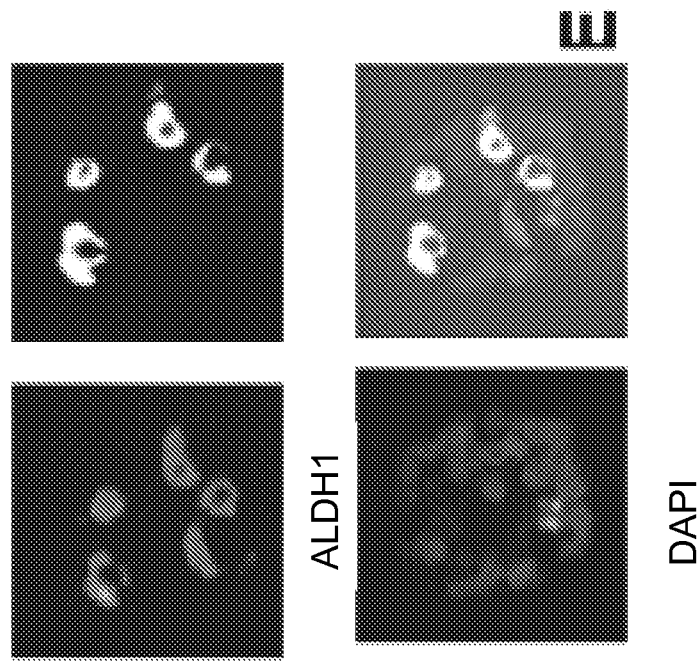
Figure 4:
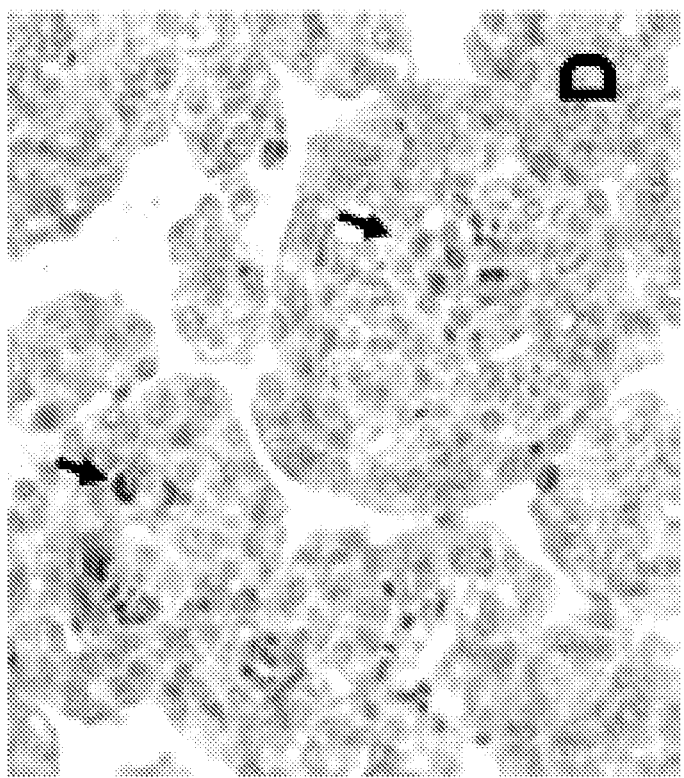

The results, shown in FIG. 4A indicate that the enzymatic ALDH positive population identified by immunostaining is contained in the ALDH positive population identified by enzymatic assay, as expected. Using the ALDH1 antibody, sections of paraffin embedded normal breat (from mammoplaties performed for esthetic reasons) were immunostained, which identified a relatively small population of cells located mostly towards the end of the acini at the bifurcation of side branches and in both luminal and basal location in mammary ducts (FIG. 4 and data not shown). ALDH1 positive cells were detected in 2 out of 10 normal breast reduction samples analyzed. Even when located in the luminal layer, the ALDH 1 positive cells did not stain with cytokeratin 8/18, a marker of luminal epithelial cells (C). This indicates that ALDH+ cells are not mature luminal epithelial cells.

It has been previously shown that the mammospheres are predominantly composed of progenitor cells. However, the mammosphere-initiating population, capable of survival and self-renewal in suspension culture, represents only a minority of the total cell population in the mammospheres (only 1-2 cells in a mammosphere). Data from serial passages of cells in suspension culture, as mammospheres, are consistent with the notion that the sphere-initiating cells are the stem cells. Immunostaining of sections through paraffin embedded mammospheres showed that the ALDH1 positive cells are present in small numbers in the mammospheres (FIG. 4 A), they co-localize with cytokeratin 5/6 (FIG. 4 B) and cytokeratin 14 (data not shown), and they do not co-localize with cytokeratin 18. Cytokeratin 5/6 and 14 are candidate breast stem cell marker (see, Gudjonsson et al., Genes & Dev. 16:693-706, 2002; and Otterback et al., Histopathology, 37(3):232-40, 2000, both of which are herein incorporated by reference). The ALDH+CK14+ cells represent a fraction of the CK14+ cells and of the CK5/6+ cells (data not shown). These results indicate that ALDH+ cells represent stem/early progenitors of the normal human breast epithelium.

Example 4

Figure 5:
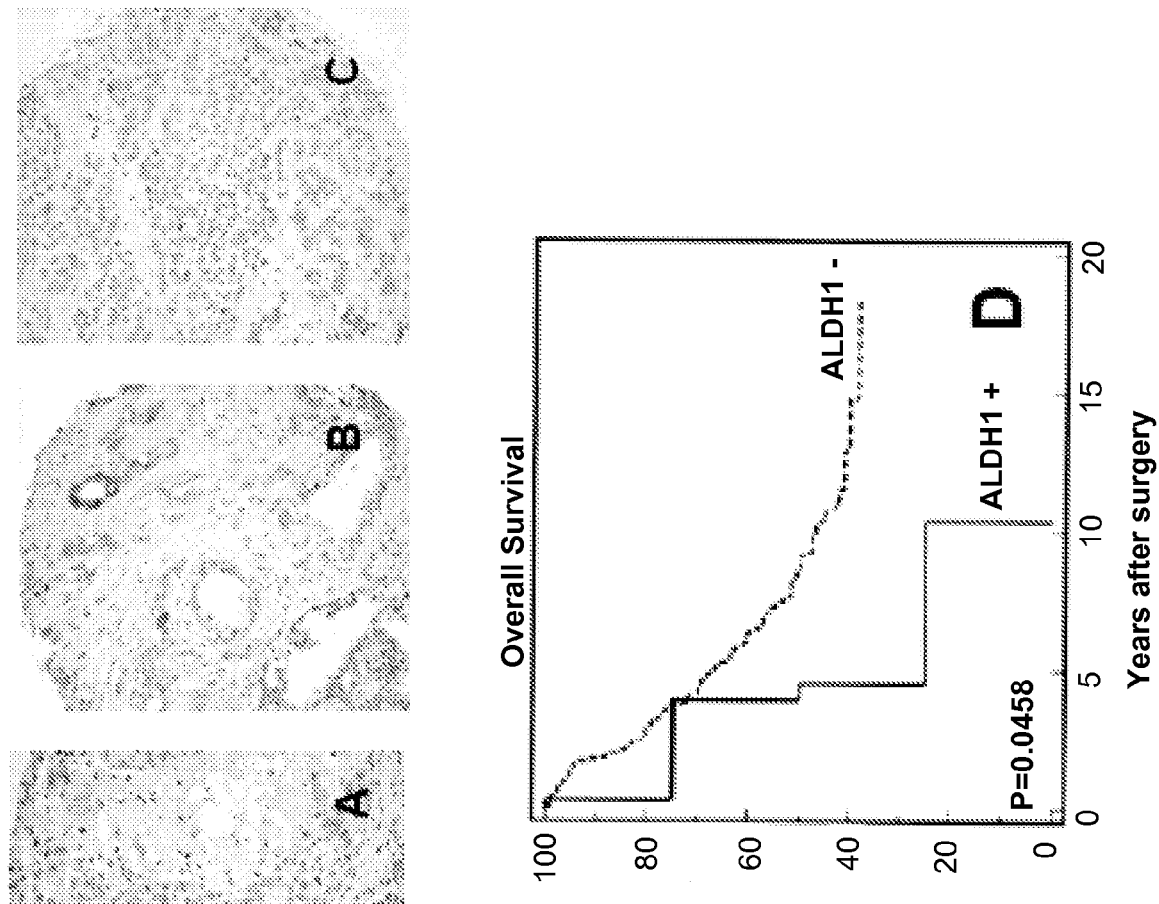
FIG. 5 shows examples of TMA breast carcinoma positive (A, B) and negative (C) for ALDH1 expression.

Immunohistochemistry on Tissue Microarrays (TMA) and Correlation With Histoclinical Parameters To assess the potential use of ALDH1 as a tumoral biomarker, expression of ALDH1 in 270 human breast carcinomas was analyzed by immunohistochemistry (IHC) on tissue microarrays (TMAs), procured from the Tissue Microarray Core Laboratory at University of Michigan Medical School (TMA1). The tumors on these TMAs represent nonconsecutive cases of breast cancers diagnosed and treated at the University of Michigan Hospital over a period of 10 years. Of the 270 tumors screened, 232 were available for IHC analysis. It was determined that 56 tumors (24%) had ALDH1 expression and 176 (76%) had no ALDH1 expression (FIG. 5 A-C).

Figure 6:
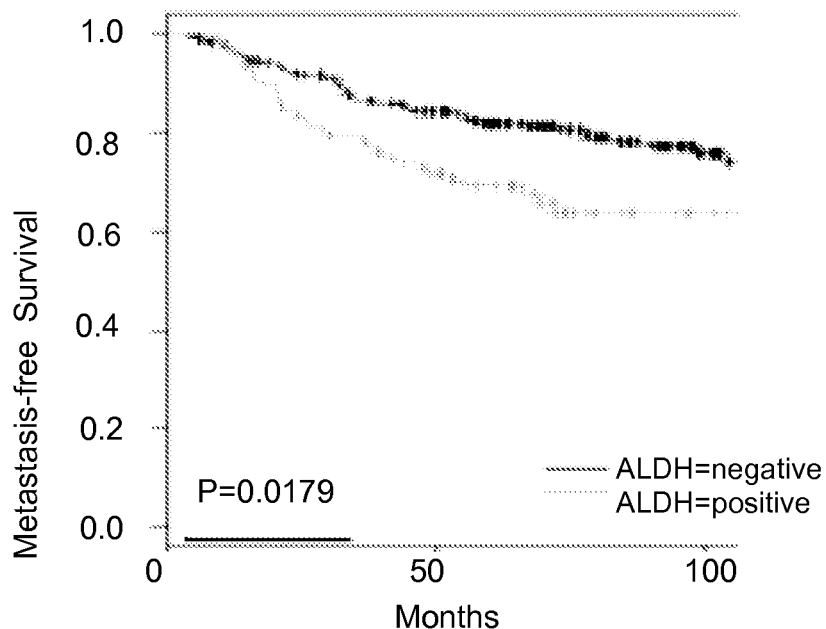
FIG. 6 shows a Kapplan-Meyer analysis according to the ALDH1 status corresponding to Example 4, with FIG. 6A depicting metastasis-free survival, and FIG. 6B B showing overall survival.
Figure 6:
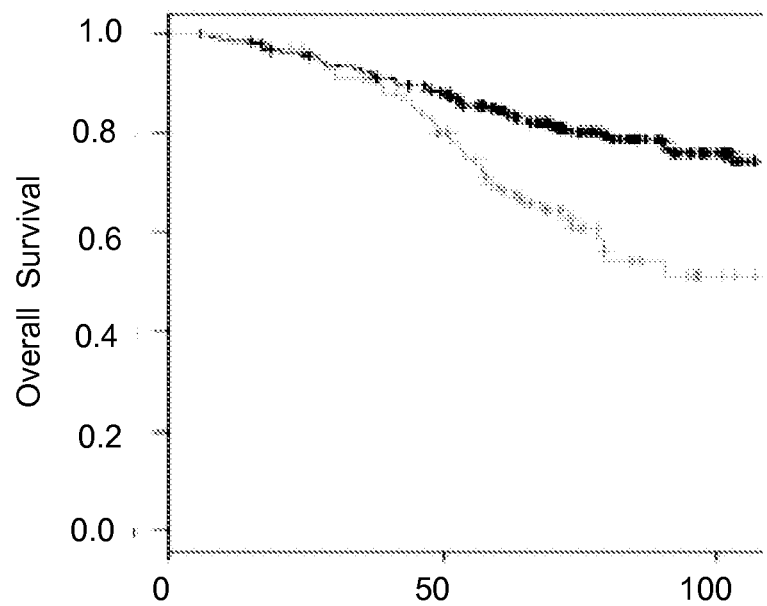
Figure 6:
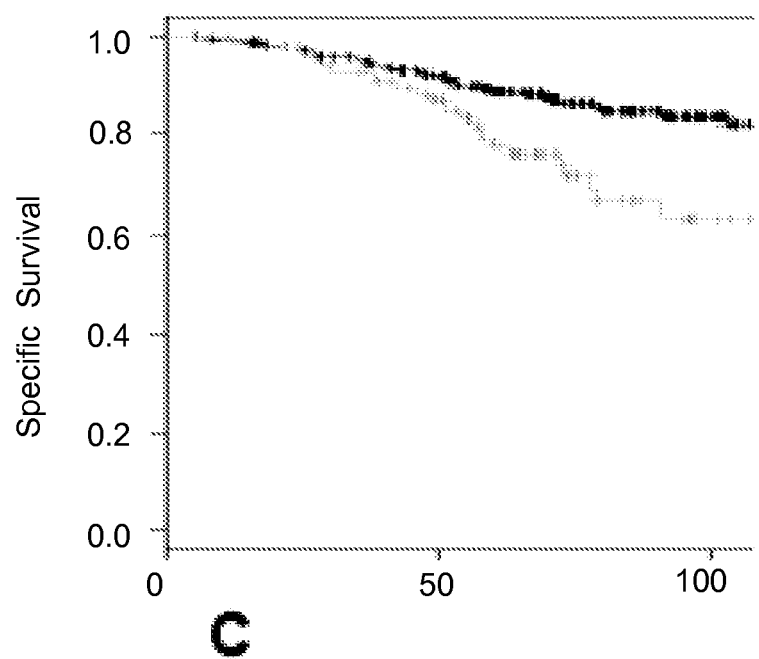

Consistent with the idea that cancer stem cells represent a minority of the tumor population, ALDH+ cells were present in small numbers in the cores analyzed. ALDH1 positive tumors were associated with lymph node metastasis ($p<0.05$, Fisher's exact test), high histological grade ($p<0.05$, Fisher's exact test), and ERBB2 overexpression ($p<0.05$, Fisher's exact test) (Table 1). No correlation was found with tumor size, age, estrogen and progesterone receptor status. Analysis of overall survival (OS) showed an association of ALDH1 positive tumors with poor prognosis (p=0.045, log-rank test) (FIG. 5.D). Another TMA produced at the Institute de Cancerologie de Marseille, Inserm, France were analyzed for ALDH1 staining (TMA2). These TMAs contain tumors from 552 consecutive patients with early (stage I, II, or III) breast cancer diagnosed and treated over a period of 12 years. Among the 552 tumors, 345 were available for IHC analysis. Similar results as in the first TMA analysis were obtained. (FIG. 6, A-C and Table 2). A strong correlation between the presence of ALDH1 and the negativity of estrogen receptor and progesterone receptor was found for the population represented on the TMA2 but not the TMA1. The difference between the two populations is probably due to the fact that the breast carcinomas from TMA 1 represent a non-consecutive population.

TABLE 1

Correlation of ALDH1 expression with histoclinical characteristics of Breast Carcinomas from American Paitents

| Characteristics | ALDH1 Negative No. of patients | (%) | ALDH1 Posittive No. of patients | (%) | p-value |
|---|---|---|---|---|---|
| All cases | 176 | (76) | 56 | (24) | |
| Age (years) | | | | | |
| ≦50 | 60 | (34) | 18 | (32) | NS |
| >50 | 116 | (66) | 38 | (68) | |

TABLE 1-continued

Correlation of ALDH1 expression with histoclinical characteristics of Breast Carcinomas from American Paitents

| Characteristics | ALDH1 Negative No. of patients | (%) | ALDH1 Posittive No. of patients | (%) | p-value |
|---|---|---|---|---|---|
| Pathological tumor size | | | | | |
| pT1 | 89 | (57) | 24 | (48) | NS |
| pT2 | 61 | (39) | 22 | (44) | |
| pT3 | 1 | (4) | 4 | (8) | |
| SBR grade | | | | | |
| I | 27 | (16) | 4 | (8) | <0.05 |
| II | 81 | (49) | 32 | (64) | |
| III | 58 | (35) | 14 | (28) | |
| Lymph node metastasis | | | | | |
| Negative | 74 | (50) | 17 | (34) | <0.05 |
| Positive | 74 | (50) | 33 | (66) | |
| Estrogen receptor | | | | | |
| negative | 45 | (27) | 11 | (21) | NS |
| positive | 120 | (73) | 40 | (89) | |
| Progesterone receptor | | | | | |
| negative | 61 | (37) | 17 | (33) | NS |
| positive | 105 | (63) | 34 | (66) | |
| ERBB2 receptor | | | | | |
| Negative(0-1) | 123 | (80) | 29 | (66) | <0.05 |
| Positive(2-3) | 31 | (20) | 15 | (34) | |

TABLE 2

Correlation of ALDH1 expression with histoclinical characteristics of breast carcinomas from French patients

| Characteristics | | ALDH1 neg (243) No. of patients (%) | ALDH1 pos (102) No. of patients (%) | p-value |
|---|---|---|---|---|
| Age, years | <=50 | 79 (35) | 25 (25) | NS |
| | >50 | 164 (65) | 77 (75) | |
| Histological type | ductal | 179 (74) | 77 (75) | NS |
| | lobular | 27 (10) | 13 (13) | |
| | medullary | 1 (1) | 3 (3) | |
| | other | 36 (15) | 9 (9) | |
| Pathological tumor size (pT) | pT1 | 103 (42) | 37 (37) | NS |
| | pT2 | 108 (45) | 46 (47) | |
| | pT3 | 30 (13) | 16 (16) | |
| SBR grade | I | 80 (33) | 24 (24) | 1.82E−04 |
| | II | 120 (49) | 38 (38) | |
| | III | 43 (18) | 39 (38) | |
| Peritomoral vascular invasion | Negative | 155 (64) | 56 (61) | NS |
| | Positive | 88 (36) | 46 (39) | |
| Axillary lymph node | Negative | 134 (56) | 43 (44) | NS (0.06589) |
| | Positive | 107 (54) | 55 (56) | |
| Estrogen Receptor | Negative | 41 (17) | 39 (39) | 2.92E−05 |
| | Positive | 196 (83) | 61 (61) | |
| Progesterone Receptor | Negative | 61 (26) | 51 (52) | 1.30E−05 |
| | Positive | 170 (74) | 47 (48) | |

Example 5

Inflammatory Breast Cancer (IBC) Stem Cells Express ALDH1

Figure 7:
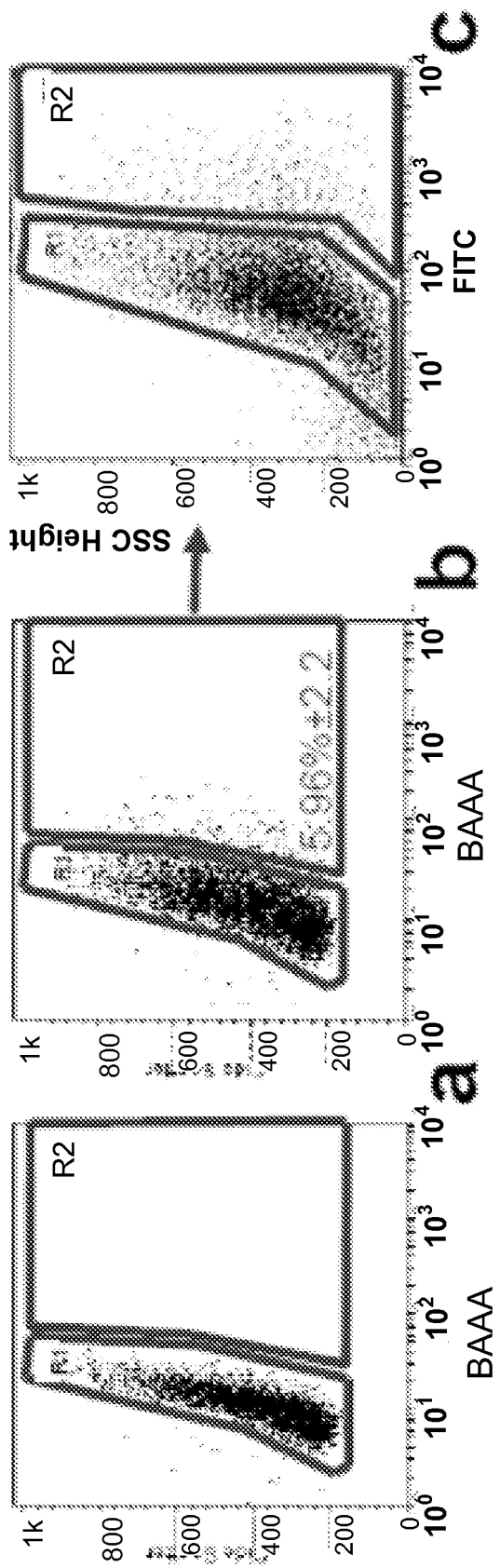
FIG. 7 shows that the ALDEFLUOR-positive cell population of SUM-149 cells displays properties of cancer stem cells and mediates invasion and metastasis.
Figure 7:
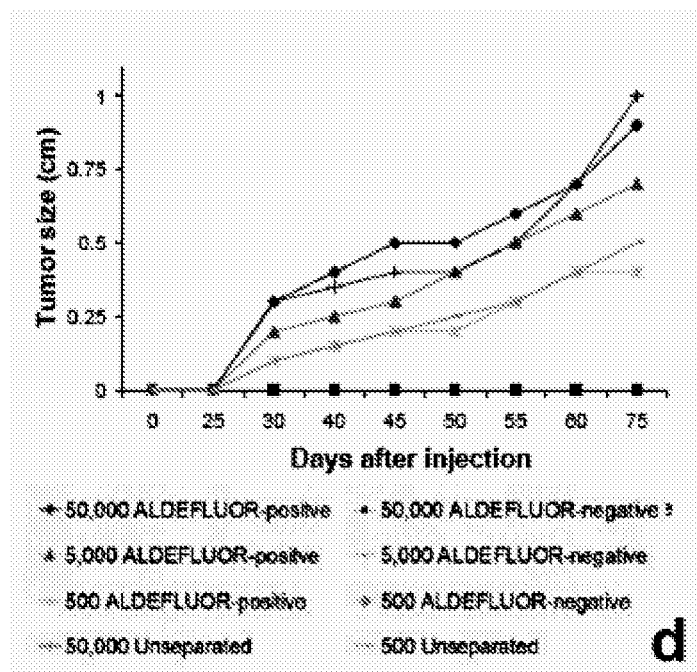
Figure 7:
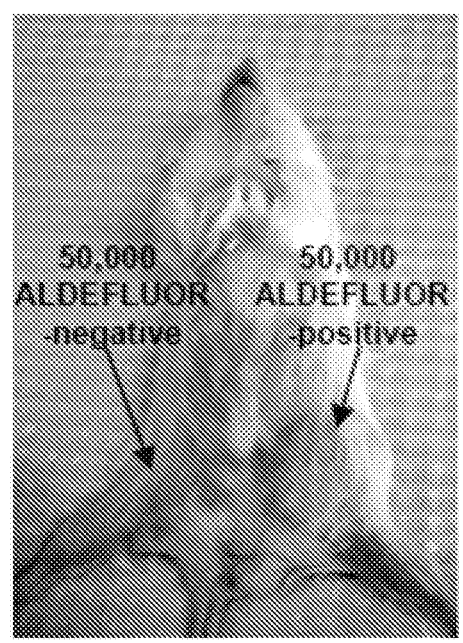
Figure 7:
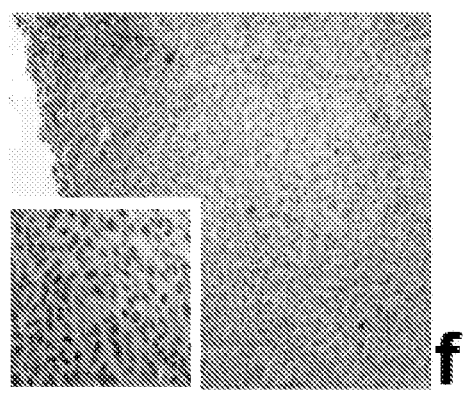
Figure 7:
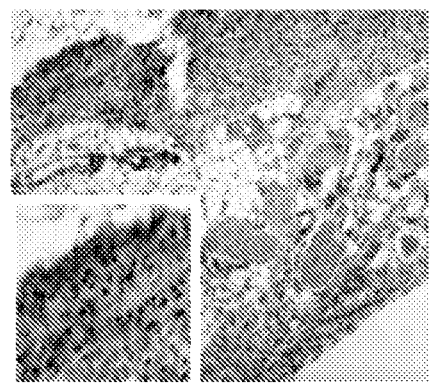
Figure 7:
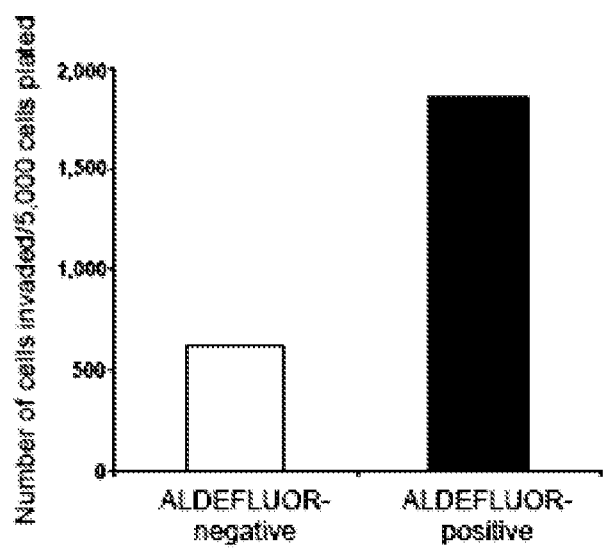
Figure 7:
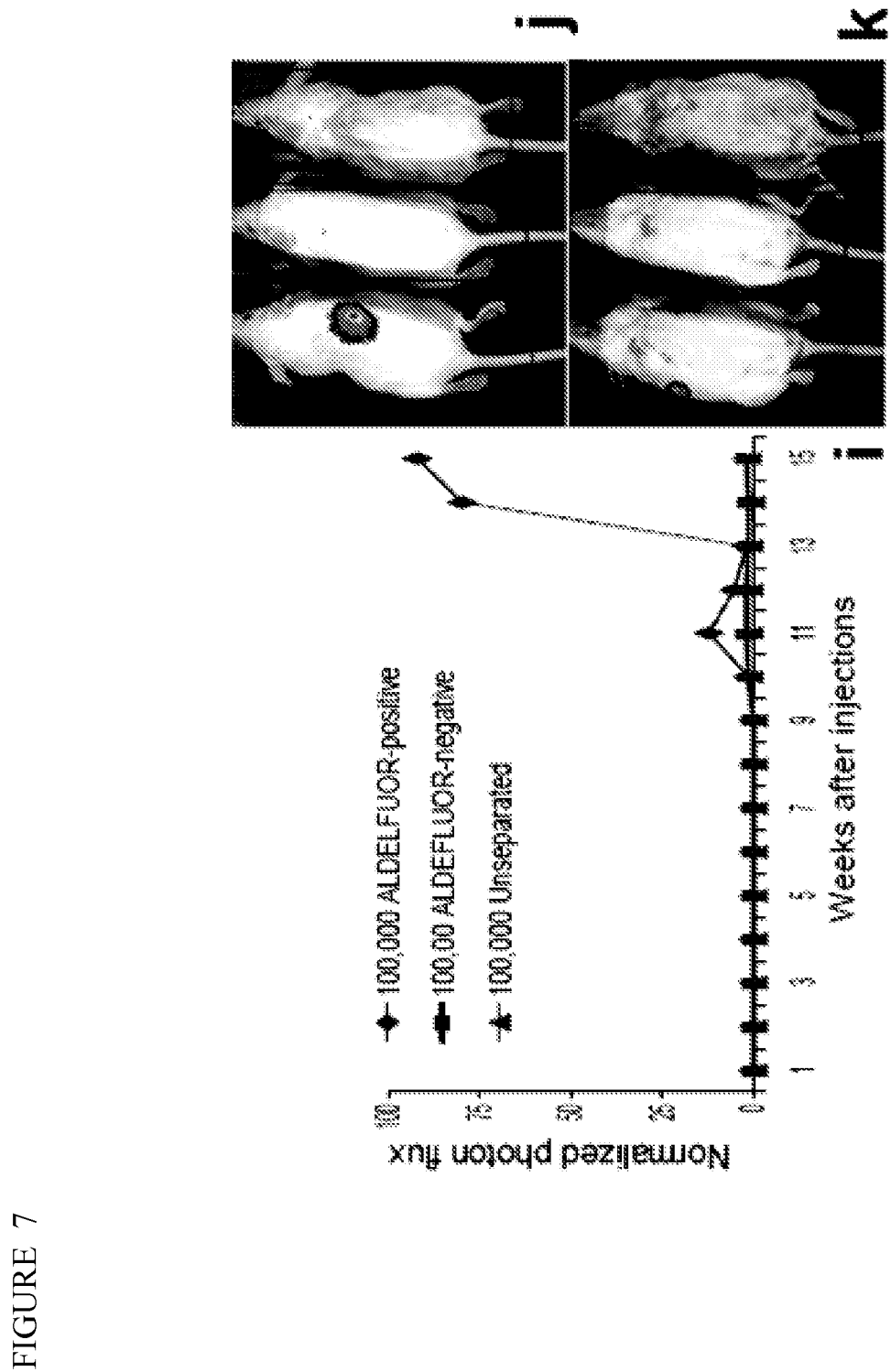
Figure 7:
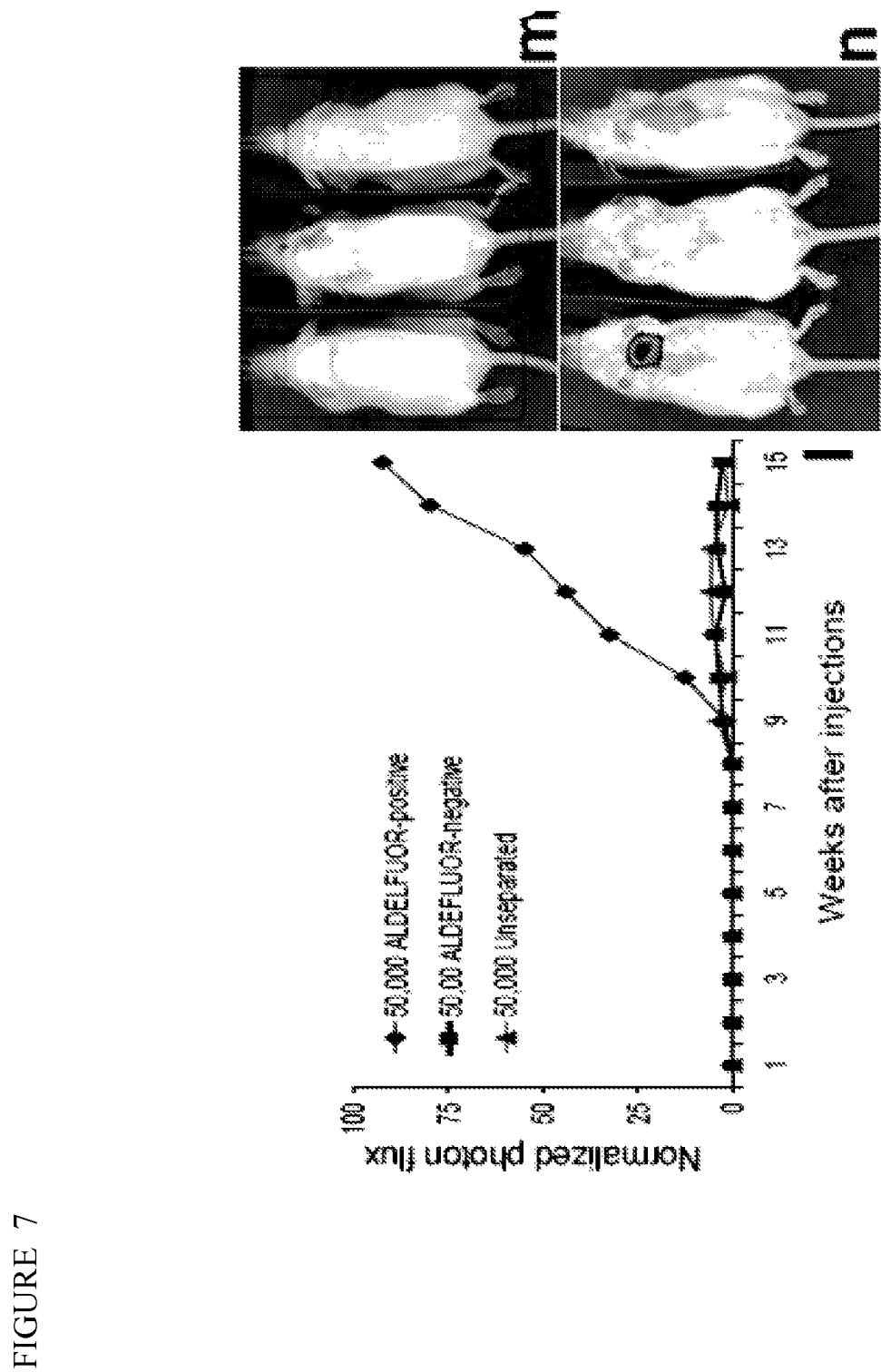
Figure 7:
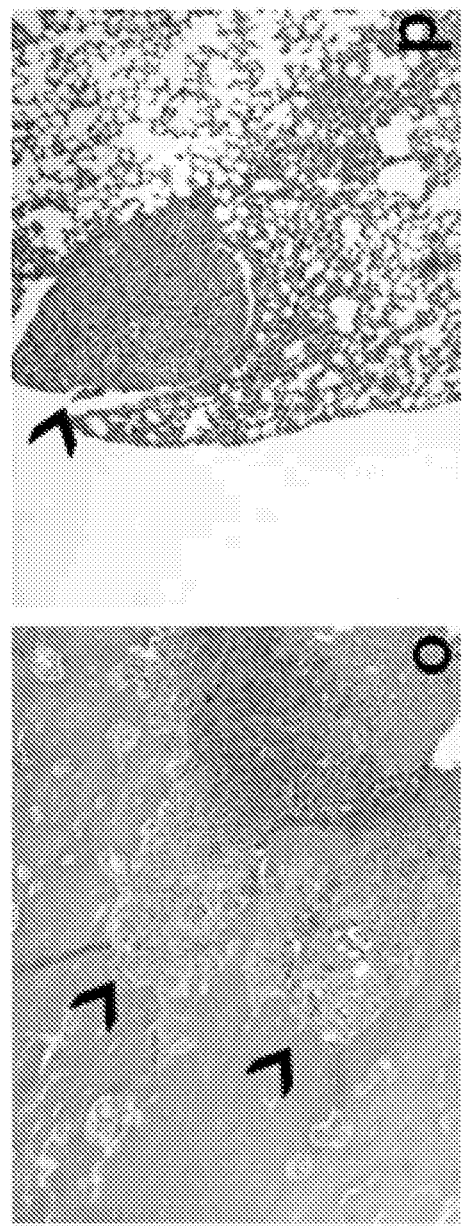

In this Example, two methods have been used to determine whether IBC contains cancer stem cells and whether these cells mediate tumor metastasis. The SUM-149 breast cancer cell line, derived from a primary IBC, was utilized (van Golen K L, et al., Clin. Cancer Res. 5, 2511-2519 (1999). The ALDEFLUOR-positive component was isolated which was 5.96±2.2% of the total cell population (FIG. 7 a-b). The tumorigenicity of the ALDEFLUOR-positive, ALDEFLUOR-negative and unseparated populations from SUM-149 cells was tested in three serial passages, using injection of limiting dilutions of cells (50,000; 5,000; 500 cells) into humanized mammary fat pads of NOD/SCID mice (Kuperwasser et al., Proc. Natl. Acad. Sci. U.S.A. 101, 4966-4971 (2004)). After 75 days, the fat pad injections with 50,000, 5,000 and 500 ALDEFLUOR-positive cells generated tumors whereas the ALDEFLUOR-negative cells failed to do so even when 50,000 cells were inoculated (FIG. 7 d-g).

H&E staining of fat pad sections confirmed that tumors formed by ALDEFLUOR-positive cells contained malignant cells (FIG. 7D whereas only residual Matrigel, apoptotic cells and mouse tissue were seen at the sites of the ALDEFLUOR-negative cell injections (FIG. 7g). As indicated in FIG. 7d, the size and latency of tumor formation correlated with the number of ALDEFLUOR-positive cells injected, with 500 ALDEFLUOR-positive cells generating tumors in 30 days. Similar results were obtained for all three consecutive passages performed in NOD/SCID mice.

The ability of a small number of ALDEFLUOR-positive cells to generate tumors that could be serially passaged demonstrates the capacity of these cells to self-renew. In addition to self-renewal, stem cells are also have the ability to differentiate into the cells forming the bulk of the tumor. As shown in FIG. 7c, ALDEFLUOR-positive cells generated tumors that contained ALDEFLUOR-positive and -negative cells in a similar proportion to that found in the initial tumor. This indicates that the ALDEFLUOR-positive cells are able to self-renew as well as differentiate, which indicates that this a tumor stem cell population.

IBC has a high propensity for lymphagenic invasion and distant metastasis. To assess the propensity of inflammatory carcinoma stem cells to invade, a Matrigel invasion assay was utilized. The percent of ALDEFLUOR-positive SUM-149 cell population capable of invasion through Matrigel was three-fold higher than that of the ALDEFLUOR-negative population (FIG. 7 h). To determine the metastatic capacity of ALDEFLUOR sorted cells, SUM-149 cells were labeled with a luciferase lentivirus reporter system. The luciferase-labeled cells were sorted using ALDEFLUOR and the ALDEFLUOR positive, -negative and unseparated cells were used for intra-cardiac injections in NOD/SCID mice. A suspension of 50,000 and 100,000 cells from each group were injected into three mice and the development of metastasis was assessed by non-invasive luciferase bioluminescence imaging quantified by photon flux (Minn et al., Proc. Natl. Acad. Sci. U.S.A, 104, 6740-6745 (2007)). As shown in FIG. 7 i-n, only the ALDEFLUOR-positive cells formed metastases. Histologic sections confirmed the presence of both bone and lung metastases (FIG. 7 o-p). In contrast, no metastases were detected in mice inoculated with 100,000 or 50,000 ALDEFLUOR-negative or unseparated cells. The absence of systemic metastasis was confirmed by histologic examination of sections through the liver, bone, brain and lung tissues.

Figure 8:
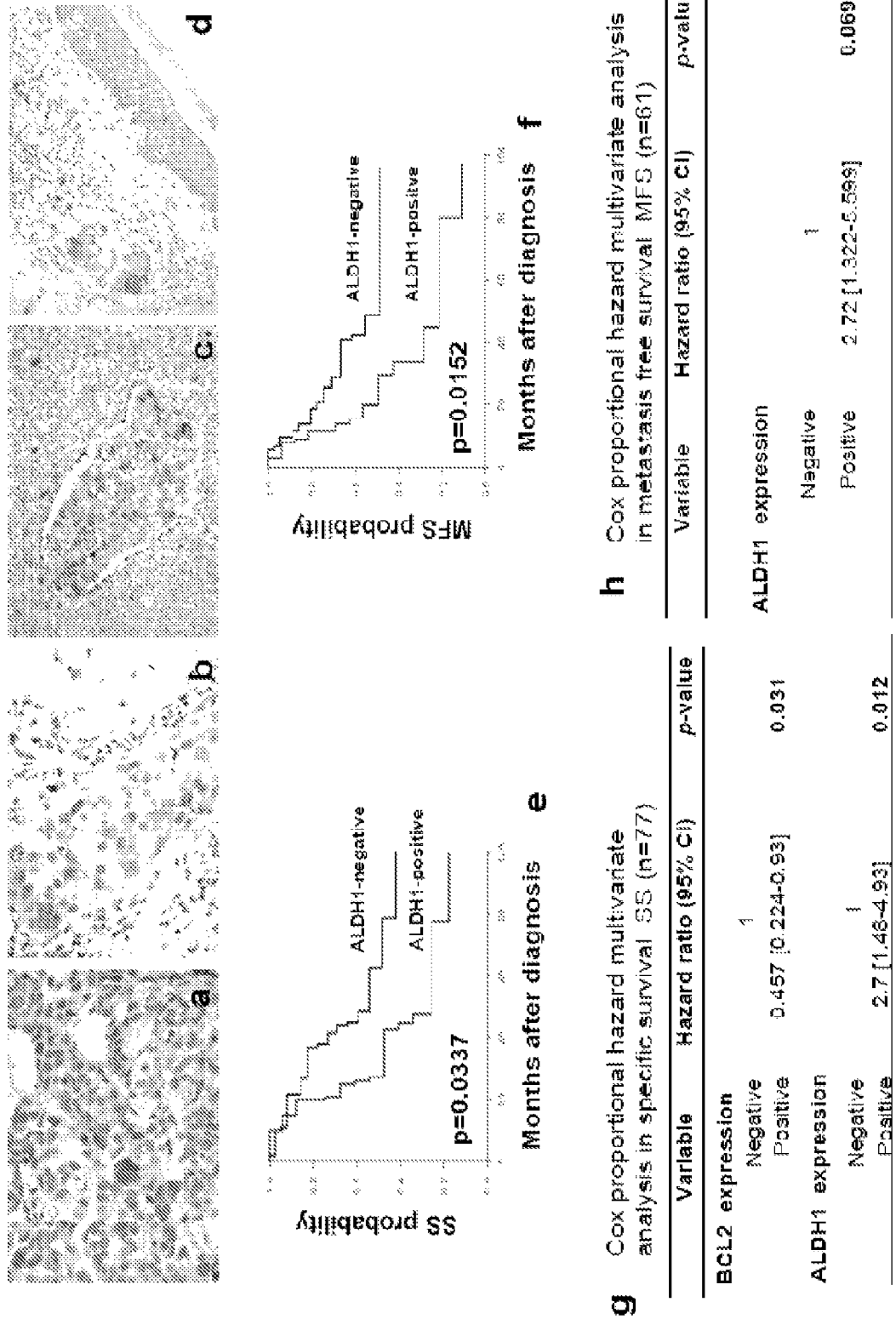
FIG. 8 shows ALDH1 expression in IBC patient tumors is associated with development of metastasis and decreased survival.

These results indicate that local invasion and systemic metastasis in inflammatory breast cancer may be mediated by cells expressing ALDH1. As shown in previous Examples have demonstrated, antibodies to ALDH1 can detect cancer stem cells in situ. The expression of ALDH 1 was examined in a series of 109 IBC patients. ALDH 1 was expressed in 34% of tumors with an average expression of less than 5% of positive cells (FIG. 8 a). This percentage of ALDH1 expression is similar to that found in non-inflammatory breast cancer. ALDH1 positive cells were also detected in intralymphatic tumor emboli (FIG. 8 b-d). ALDH 1 expression correlated with the SBR grade, as previously observed in noninflammatory breast cancers. There was no other correlation with clinical or pathologic features including estrogen and progesterone receptors, BCL2, ERBB2, E-cadherin or MUC1.

Kaplan-Meier survival curves were constructed and compared by log-rank tests to determine whether the expression pattern of the stem cell marker ALDH1 in IBC correlated with survival of breast cancer patients. ALDH1 expression correlated with survival as well as the development of distant metastasis in IBC. The median follow-up of all patients was 67 months. As shown in FIG. 8 e-f, ALDH1 expression was strongly correlated with tumor-specific survival (SS) as well as metastasis-free survival (MFS) (pSS=0.0337 and pMFS=0.0152). Median SS was 63 months for patients whose tumors did not express ALDH1 compared to only 27 months for patients with tumors expressing ALDH1. Median MFS was 49 months in patients with ALDH-negative tumors, compared to 20 months in patients with ALDH-positive tumors.

Multivariate analysis using Cox proportional hazard models showed that ALDH1 is the most powerful prognostic marker of SS (ALDH1: p=0.0012, HR=2.7, 95% Cl [1.48-4.93]; BCL2: p=0.031, HR=0.457, 95% CI [0.0224-0.93]) and the only prognostic marker of MFS (p=0.0055, HR=2.81, 95% Cl [1.355-5.815]) when factors significant in univariate analysis (hormonal receptor and BCL2 expression) were included in the model (FIG. 8 g-h).

The above Example demonstrates that ALDH-expressing IBC cells have properties of cancer stem cells, are highly invasive, and are able to mediate metastasis in NOD/SCID mice. This Example also shows that the expression of the stem cell marker ALDH1 can predict metastasis and overall clinical outcome in patients with inflammatory breast carcinoma.

Example 6

BRCA1 Regulates Human Mammary Stem/Progenitor Fate

This example provides evidence that BRCA1 is involved in regulating the differentiation of ALDH1-positive/ER-negative stem/progenitor cells into ER-positive epithelial cells.

Materials and Methods

Dissociation of mammary tissue and mammosphere culture. 100-200 g of normal breast tissue from reduction mammoplasties was minced with scalpels, dissociated enzymatically, and single cells were cultured in suspension as described previously (Dontu et al., (2004) Breast cancer research: BCR. 6(6); and Liu et al., (2006) Cancer Res 66(12), 6063-6071). Mammospheres were dissociated into single cells enzymatically and mechanically, and then cultured in suspension to produce mammospheres or induced to differentiate on a collagen substratum.

Differentiating culture conditions. Single cell suspensions were plated on collagencoated plates at a density of 5000 viable cells/10 cm diameter dish. Cells were grown in Ham's F-12 medium (GIBCO™ INVITROGEN) with 5% fetal bovine serum (FBS), 5 µg/ml insulin, 1 µg/ml hydrocortisone, 10 µg/ml cholera toxin (Sigma, St Louis, Mo., USA), 10 ng/ml epidermal growth factor (BD Biosciences) and 1× Pen/Strep/Fungizone Mix (GIBCO). Cells were collected for the lineage analysis by FACS at different time points (Day 0, Day 7, Day 12, Day 26, Day 35).

Real-time RT-PCR. After mammospheres were formed in suspension culture or cells reached 85% confluency on the collagen plates (about 7 d), total RNA was isolated using RNeasy Mini Kit (QIAGEN) and utilized for real-time quantitative RT-PCR (qRTPCR) assays in a ABI PRISM® 7900HT sequence detection system with 384-Well block module and automation accessory (Applied Biosystems).

Western blotting. Cells were lysed using Pierce Nuclear and Cytoplasmic Extraction Reagent Kit (Pierce Biotechnology, Rockford, Ill.). Samples were normalized for protein concentration using Pierce BCA Protein Assay. 50 µg of each nuclear extract sample was analyzed by 5% SDS-PAGE, and transferred to a polyvinylidene difluoride (PVDF) membrane. Immobilized proteins were probed using antibodies specific for BRCA1 (Ab 4, Oncogene research, San Diego, Calif.), or actin (Santa Cruz Biotechnology) and visualized by enhanced chemiluminescence (Amersham Pharmacia Biotech, Piscataway, N.J.).

Aldefluor assay and flow cytometry. Single cells were isolated from lentivirus-infected primary mammospheres and the ALDEFLUOR kit (StemCell technologies Inc, Vancouver, BC, Canada V5Z 1B3) was used to isolate cells with high ALDH enzymatic activity as illustrated in the manufacturer's instructions. Briefly, single cells were suspended in ALDEFLUOR assay buffer containing ALDH substrate-BAAA (1 µmol/l per 1×106 cells) and incubated at 37° C. for 40 minutes. In each experiment, the specific ALDH inhibitor diethylaminobenzaldehyde (DEAB) was used as negative control at 50 mmol/L. A FACStarPLUS (Becton Dickinson) was used for FACS. ALDEFLUOR fluorescence was excited at 488 nm and fluorescence emission was detected using a standard fluorescein isothiocyanate (FITC) 530/30 band pass filter. The sorting gates were established based on the negative controls. 1 µg/ml propidium iodide (PI) (Sigma) was used to access cell viability.

For flow cytometry analysis, freshly dissociated cells cultured on collagen substrata were stained with PE-conjugated ESA (dilution 1:100, Miltenyi Biotec, Auburn, Calif.) and PE-cy5-conjugated CD10 (dilution 1:25, Novocastra, Newcastle, UK) in Hanks Balanced Salt Solution (HBSS, GIBCO) with 2% FBS and incubated on ice for 20 min., followed by washing in HBSS with 2% FBS and resuspending in HBSS supplemented with 2% FBS with 1 µg/ml propidium iodide (PI) (Sigma) for the cell viability. Analysis was performed using FACStarPLUS (Becton Dickinson, Palo Alto, Calif., USA) flow cytometer.

Immunostaining. Paraffin-embedded tissue sections were deparaffinized in xylene and rehydrated in graded alcohol. Antigen retrieval was performed by incubating the sections in citrate buffer pH 6.0 (Zymed, South San Francisco, Calif.) at 98° C. for 40 minutes. Staining was done using a Peroxidase histostain-Plus Kit (Zymed, South San Francisco, Calif.) according to the manufacturer's protocol. The primary antibodies, ALDH1 (BD Transduction Laboratories), cytokeratin 18 (Novocastra), cytokeratin 14 (Novocastra), Smooth muscle actin (SMA) (DAKO), estrogen receptor (NeoMarkers), and GFP (NeoMarkers) were used at the dilutions indicated by the manufacturer. AEC and DAB (Zymed, South San Francisco, Calif.) were used as substrates for peroxidase. Slides were counter-stained with hematoxylin, and mounted with glycerin.

Laser Capture Microdissection. Laser capture microdissection (LCM) was used to obtain separate and pure cell populations from lobules expressing ALDH1 and lobules negative for ALDH1 expression. Five µm paraffin embedded sections were obtained from breast tissue from women with confirmed germline BRCA1 mutations, were immunostained for ALDH1 and LCM was performed on these stained sections. For each patient, tissue from eight serials sections were collected. The Arcturus PixCell II Laser capture microdissecting system (Arcturus Engineering Inc., Mountain View, Calif.) utilizes a transparent thermoplastic film applied to the surface of the tissue sections on histopathology slides. The ALDH1-positive and -negative normal epithelial cells to be microdissected were identified and targeted by microscope examination. A narrow (~15 µm) carbon dioxide laser-beam pulse specificity activated the film above these cells. The resulting strong focal adhesion allowed selective procurement of targeted cells.

DNA extraction. DNA from microdissected tissues was extracted using the Picopure™ extraction kit (Arcturus Engineering Inc). Microdissected tissues was incubated in 50 µl of lysis buffer at 42° C. overnight followed by heat inactivation at 95° C. for 10 min.

Markers for LOH and amplification. Four microsatellites from the BRCA1 region on chromosome arm 17q were selected (two intragenic microsatellites, D17S855, D17S1323 and two telomeric microsatellites, D17S1325, D17S806). Selection was done based upon several criteria including: localization, degree of heterozygosity, previous use in LOH studies, and efficiency of amplification of DNA from microdissected tissue. The order of the markers on the map is known precisely due to the availability of the sequence of the human genome (http:// followed by ensembl.ebi.ac.uk/; http:// followed by genome.ucsc.edu/). Primers were designed according to UniSTS Microsatellite analysis was done after amplification by PCR using a Perkin-Elmer Cetus thermal cycler model 9600 (Perkin-Elmer Cetus, Courtaboeuf, France).

Allelic profiles and LOH analysis. The resulting PCR products were visualized and analyzed with automated fluorescent sequencing apparatus (ABI 3730 Sequencer, DNA sequencing core, University of Michigan). The allelic profiles were read on computer print-outs separately by two observers, with one observer reading twice, at two intervals. For a given, informative marker, LOH was defined by a sharp decrease of either peak of more than 75%.

siRNA contructs. Two human BRCA1 siRNA oligos were purchased from Ambion, Inc (Silencer™ Pre-designed siRNAs) and were used to knockdown BRCA1 expression in primary human mammary epithelial cells. The lentiviral siRNAs were constructed and produced, and the cells were infected as described previously (Liu et al., (2006) Cancer Res 66(12), 6063-6071). In experiments, over 70% of cells in suspension culture were infected with the lentiviruses. The infected cells were sorted based on the GFP- or DsRed-positivity using FACStarPLUS (Becton Dickinson, Palo Alto, Calif., USA) flow cytometer.

NOD-SCID mouse model. The number 4 inguinal mammary glands of three-week-old female NOD-SCID mice were cleared and humanized, following a previously established protocol (Shackleton, et al. (2006) Nature 439(7072), 84-88). After about 4 weeks, a 60-day release estrogen pellet (0.72 mg/pellet, Innovative Research of America) was placed s.c.

on the back of the mouse's neck by using a trocar, and 1.2~2.0×105 single cells were resuspended in 20-50 μl of 1:1 matrigel: 5% serum Ham's F-12 and injected into each of the cleared fatpads. All of the implantation experiments were repeated 3 times (at least two mice each time) utilizing single cells obtained from different patients. 2-3 months after the implantation, the fatpads were removed and fixed in 10% formalin. The tissue was then embedded in the paraffin and sectioned.

Results and Discussion

Figure 9:
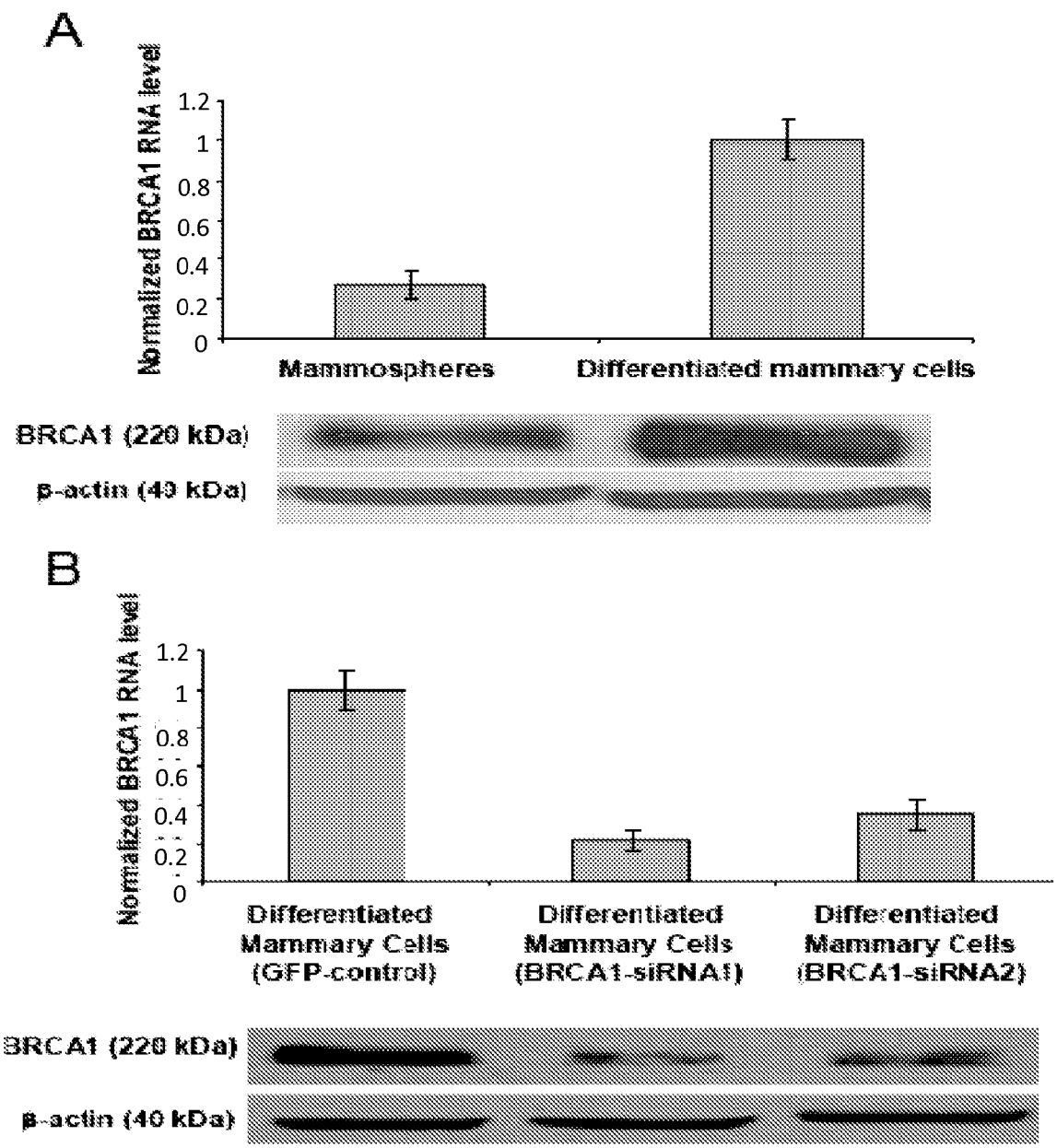
FIG. 9 shows that BRCA1 expression increases during mammary differentiation. Knockdown of BRCA1 increases mammary stem/progenitor cells and, decreases ER expression. A. Level of BRCA1 mRNA and protein in mammospheres compared to attached (differentiated) cells measured by Real-time RT-PCR and western blot, respectively. B. Level of BRCA1 mRNA and protein measured by Real-time RT-PCR and western blot in BRCA1 knockdown mammary epithelial cells compared to GFP-control infected mammary epithelial cells. Two independent BRCA1 siRNA lentiviruses were utilized and a GFP-control lentivirus to infect the cells. C. BRCA1 knockdown increases mammosphere number upon serial passage. D. ALDH 1 enzymatic activity as assessed by the ALDEFLUOR assay and flow cytometry demonstrates that BRCA1 knockdown increases the ALDE-FLUOR-positive population in vitro. E. As assessed by flow cytometry, BRCA1 knockdown decreases ER expression in BRCA1 knockdown cells compared to DsRed-control primary mammary epithelial cells. SUM-44 ER-positive and SUM-159 ER-negative breast cancer cell lines serve as positive and negative controls.
Figure 9:
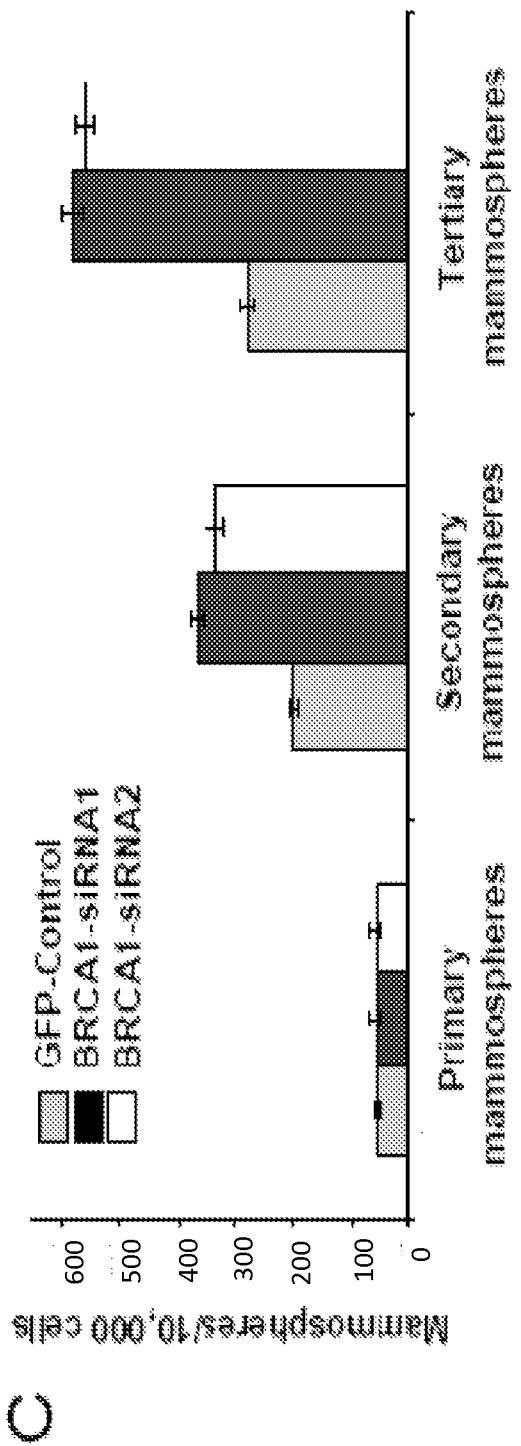
Figure 9:
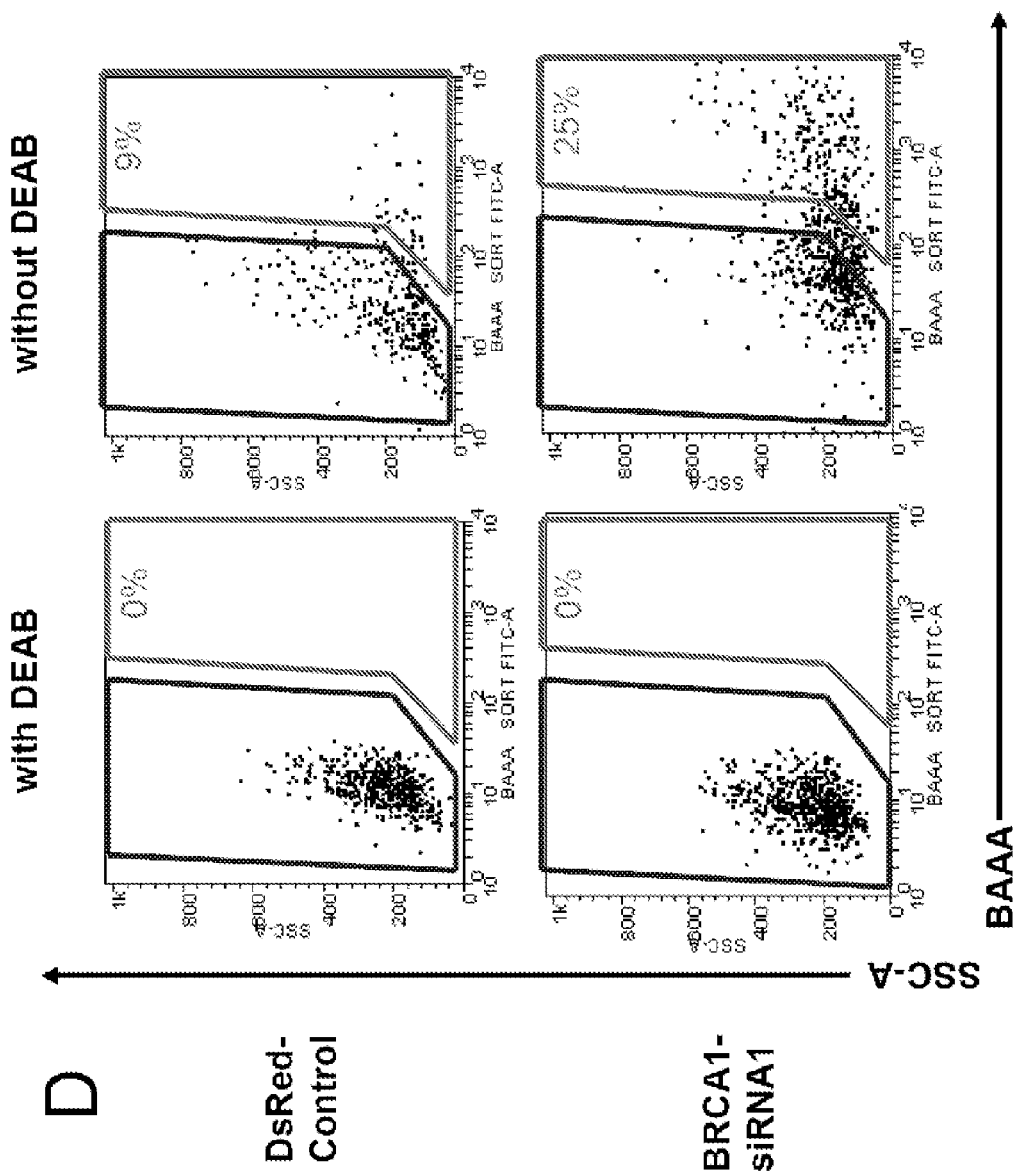
Figure 9:
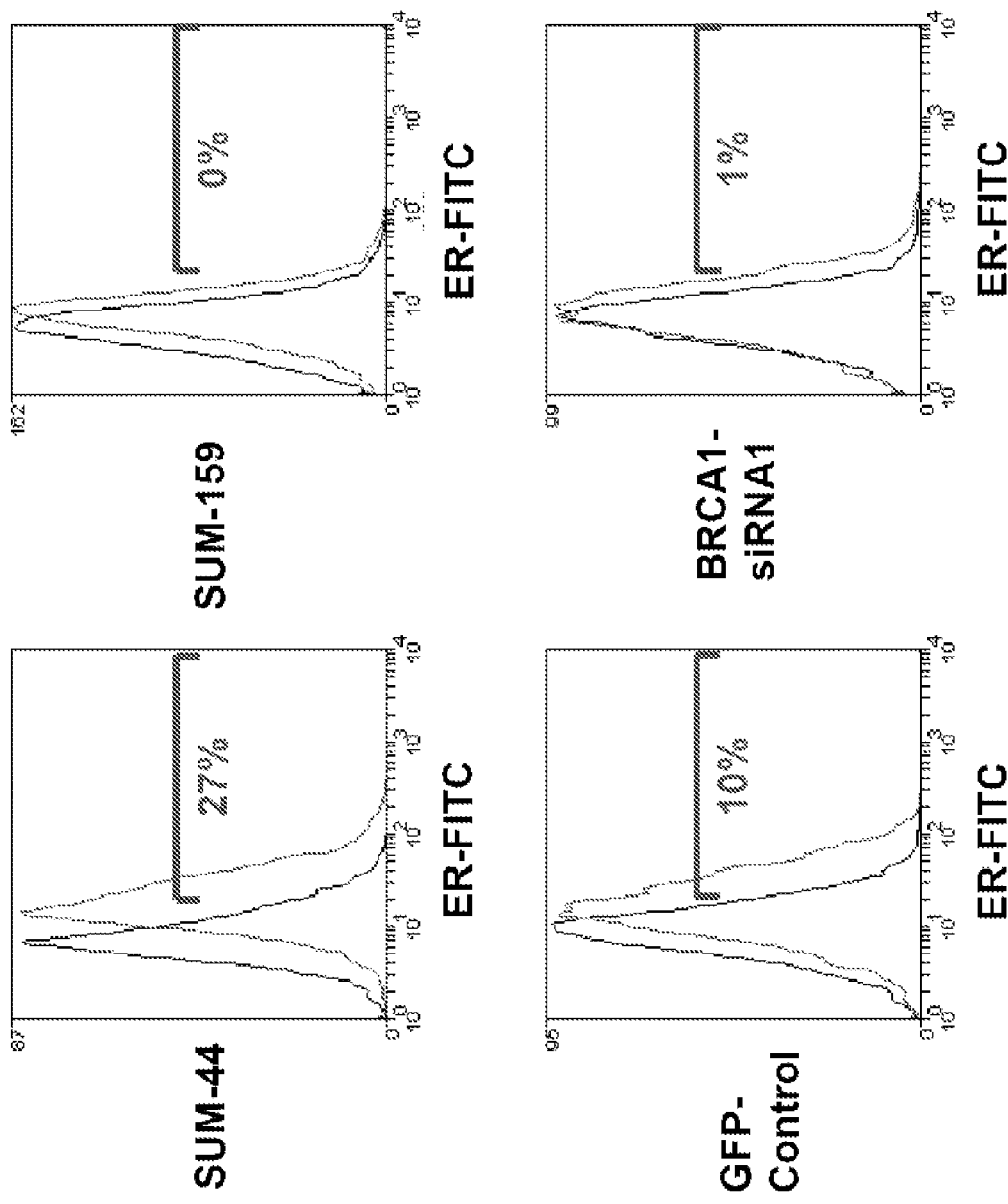

In order to elucidate the role of BRCA1 in mammary stem cell self-renewal and differentiation, an in vitro system was utilized in which primitive mammary stem/progenitor cells can be propagated in culture as floating spherical colonies termed mammospheres. Mammospheres contain a small number of ALDH1-positive cells capable of self-renewal as well as multi-potent progenitor cells capable of differentiation into luminal epithelial cells and myoepithelial cells. When mammospheres are induced to differentiate by attachment to collagen coated dishes, the level of BRCA1 increases approximately four-fold at both the mRNA and protein level (FIG. 9A). In order to determine whether BRCA1 plays a direct role in mammary stem cell self-renewal and differentiation, BRCA1 siRNA lentiviruses was utilized to knockdown BRCA1 expression in primary mammary cells and the effect on mammary stem cell self-renewal and differentiation was examined. As shown in FIG. 9B, two independent BRCA1 siRNA lentiviruses reduced BRCA1 expression by over 80% at both the mRNA and protein level compared to a GFP-control lentivirus. Knockdown of BRCA1 had no effect on primary mammosphere formation, but significantly increased secondary mammosphere formation by 70% and tertiary mammosphere formation by 100% (FIG. 9C). The number of mammospheres formed upon serial passage at clonal density reflects self renewal of primitive mammary stem and progenitors cells. As shown in the previous Examples, it has been shown that mammary stem/progenitor cells capable of self-renewal and mammosphere formation in vitro and mammary gland reconstruction in NOD/SCID mice express aldehyde dehydrogenase (ALDH) activity as accessed by the ALDEFLUOR assay. As shown in FIG. 9D, knockdown of BRCA1 in primary normal mammary cells increased the ALDEFLUOR-positive population compared to DsRed-control cells from 9 to 25%.

Previous studies in both murine and human mammary cells suggest that the most primitive stem cells do not express estrogen receptor but are capable of differentiation into ER-positive luminal epithelial cells. In order to determine whether knockdown of BRCA1 effects estrogen receptor expression, we utilized flow cytometry to quantitate ERα expression in primary human mammary cells obtained from reduction mammoplasties. This assay was validated by utilizing ER-positive SUM-44 and ERnegative SUM-159 human mammary carcinoma cell lines. As shown in FIG. 9E, knockdown of BRCA1 in primary human mammary cells reduced the percent of cells expressing ER from 10% to 1%.

Figure 10:
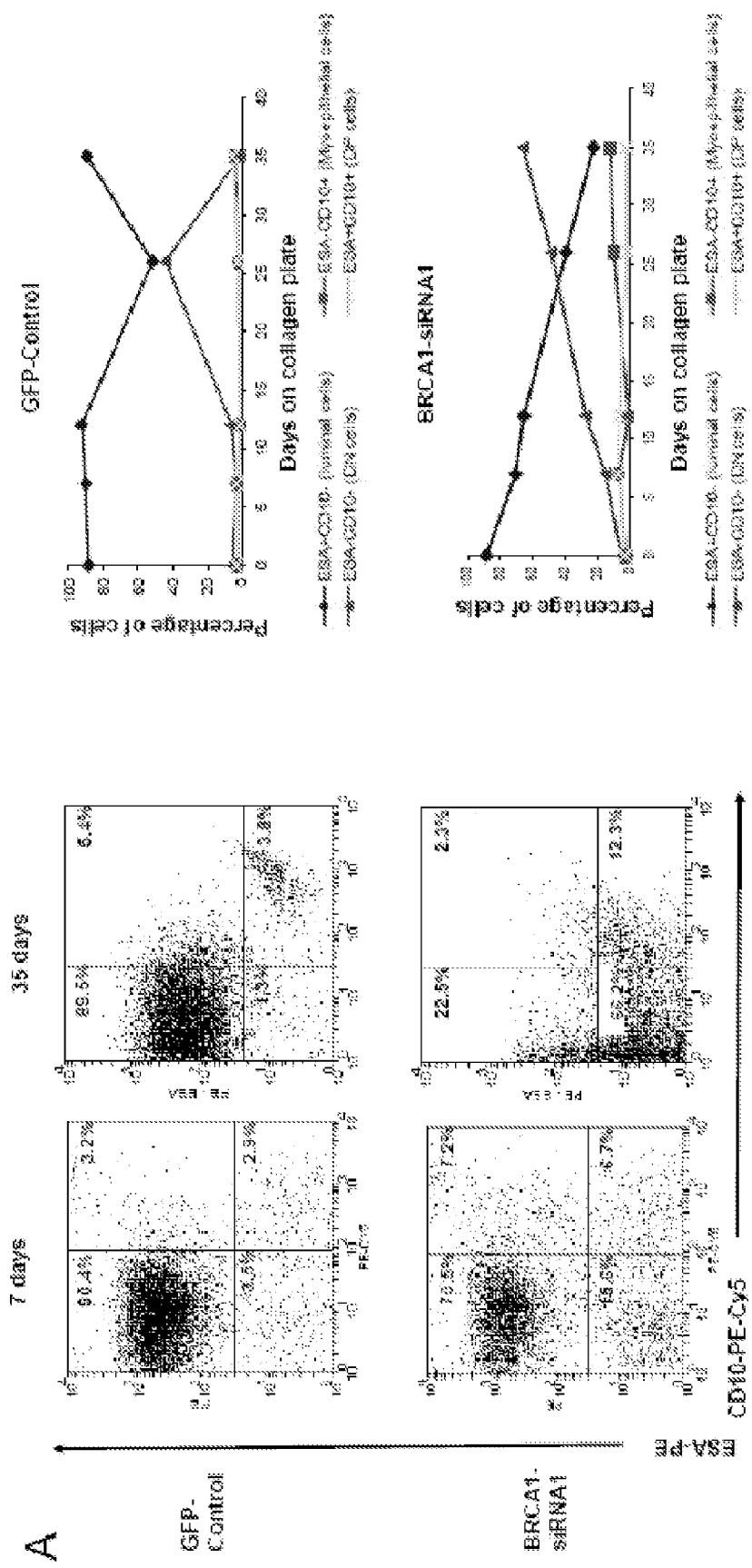
FIG. 10 shows BRCA1 knockdown blocks epithelial differentiation in vitro and in NOD/scid mice xenografts. A. Knockdown of BRCA1 blocks epithelial differentiation in vitro. Cells derived from BRCA1 siRNA or GFP-control infected mammospheres were induced to differentiate by culturing cells on collagen plates. Expression of lineage specific markers was determined by flow cytometry at different time points (0, 7, 12, 26, and 35 days). CD10 is a marker of myoepithelial cells and ESA of luminal epithelial cells. FACS analysis scatter plot according to ESA and CD10 expression are presented for the two groups, Day 0 and Day 35. Evolution of the four populations for the two groups are plotted as a function of number of culture days. B. Mammosphere initiating cells transduced with GFP-control lentivirus or BRCA1 siRNA lentivirus were introduced into the humanized cleared fat pads of NOD/SCID mice. Mammary structures formed were stained by H&E or examined by immunohistochemistry for expression of GFP, ALDH1, CK18, SMA and ER. Fatpads injected with GFP-control infected cells display mammary epithelial duct structures (i) from human origin (iii, GFP-positive, red staining) that comprised two cell layers with the inner layer expressing the luminal marker CK18 (vii, brown staining) and the outsider layer expressing the myoepithelial marker SMA (ix, red staining). No ALDH 1 expression was detected (v) and some cells display ER expression (xi, brown staining). BRCA1 knockdown cells, identified by GFP positivity (iv, red staining), produced abnormal structures composed of a single cell layer (ii) which was ALDH1-positive (vi, red staining) and negative for the expression of luminal markers CK18 (viii), and Estrogen Receptor, and with variable expression of the myoepithelial marker SMA (x, red staining).
Figure 10:
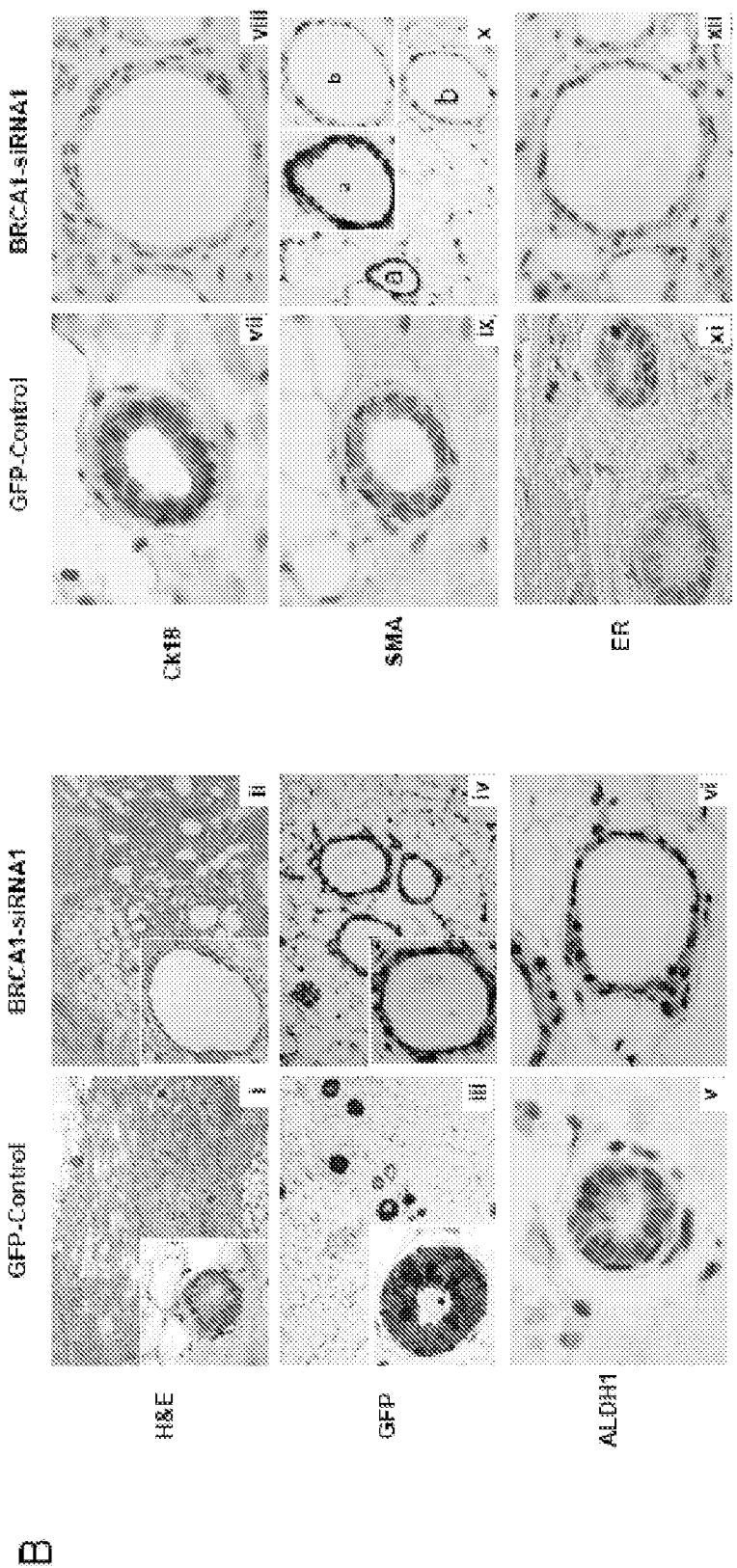

The above experiments indicate that BRCA1 is involved in the differentiation of ER-negative stem/progenitor cells to ER-positive luminal epithelial cells. In order to further elucidate the role of BRCA1 in mammary differentiation, flow cytometry was utilized with the lineage specific markers ESA (Epithelial Specific Antigen) for luminal epithelial lineage and CD10 for myoepithelial lineage. In this system, primitive doublenegative cells (DN, ESA-negative/CD10-negative) give rise to double-positive cells expressing both luminal epithelial and myoepithelial markers (DP, ESA-positive/CD10– positive), and to single-positive luminal epithelial and myoepithelial cells (ESA-positive or CD10-positive). Double-positive cells are luminal epithelial committed progenitor cells and give rise to single-positive luminal epithelial cell. BRCA1 knockdown cells cultured on collagen plates showed a significant decrease of the number of luminal epithelial cells (ESA-positive) with a significant increase in the number of undifferentiated cells (double-negative) and myoepithelial cells compared to GFP-control cells. After 35 days in culture, BRCA1 knockdown cells were composed of 65% undifferentiated cells (DN), 2% luminal epithelial committed progenitor cells (DP), 11% myoepithelial cells, and 22% luminal epithelial cells compared to GFP-control cells with 1% undifferentiated cells, 5% luminal epithelial committed progenitor cells, 4% myoepithelial cells, and 85% luminal epithelial cells (FIG. 10A).

Figure 11:
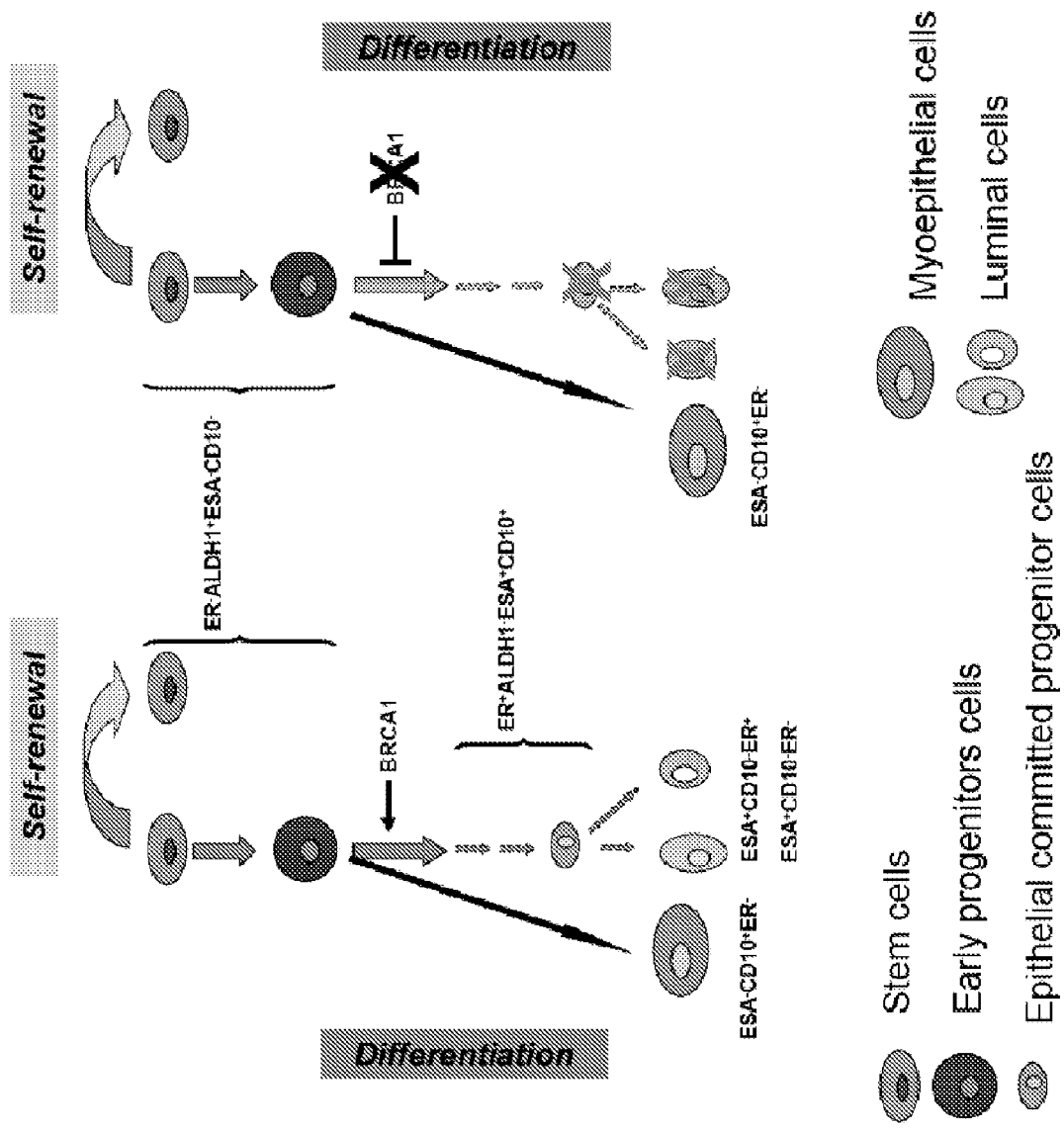
FIG. 11 shows a model depicting the proposed role of BRCA1 in mammary, stem and progenitor cell fate. BRCA1 is required for the differentiation of ALDH1-positive/ER-negative stem/progenitor cells into ER-positive luminal epithelial cells. Loss of BRCA1 function results in aberrant luminal differentiation and in accumulation of ALDH1-positive/ERnegative stem/progenitor cells.

In order to determine whether BRCA1 could effect differentiation of mammary stem/progenitor cells in vivo, a humanized NOD/SCID mouse model was utilized in which primary human mammary epithelial cells are introduced into the cleared fat pads of NOD/SCID mice whose stroma has been humanized by the introduction of mixed irradiated and non-irradiated human mammary fibroblasts. Primary mammary cells infected with GFP (GFP-control lentiviruses) or BRCA1 siRNA GFP lentivirus were introduced into these humanized mammary fat pads. After two months, mice were sacrificed and the mammary structures examined by immunohistochemistry. As shown in FIG. 10B, all of the structures produced stained positive with anti-GFP antibody demonstrating human origin and continued gene expression in these structures. All the structures produced stained positive for the pan-cytokeratin AE1/AE3 demonstrating epithelial origin of these structures (data not shown). Ductal structures generated by GFP-control cells were composed of an inner layer of CK18-positive luminal epithelial cells surrounded by a single layer of SMA-positive myoepithelial cells recapitulating the cellular organization found in normal mammary glands (FIG. 10B). In contrast, BRCA1 knockdown cells generated abnormal structures composed of a single cell layer (FIG. 10B). In some glands this single layer of cells expressed only the myoepithelial marker SMA whereas other glands were composed of cells which were negative for expression of both the epithelial marker CK18 and the myoepithelial marker SMA (FIG. 10B). Interestingly, glands produced from the BRCA1 knockdown cells but not GFP-control lentivirus, uniformly expressed the stem cell marker ALDH1 but were negative for ER expression. Thus, the knockdown of BRCA1 in this animal model produced structures displaying stem cell and differentiation markers similar to those produced by BRCA1 knockdown in vitro. Together, these in vitro and mouse model experiments indicate that BRCA1 expression is required for the differentiation of ALDH1-positive/ER-negative mammary stem/progenitor cells into ALDH1-negative/ERpositive epithelial cells. Loss of BRCA1 function results in accumulation of ALDH1-positive/ER-negative stem/progenitor cells. This model is depicted graphically in FIG. 11.

Figure 12:
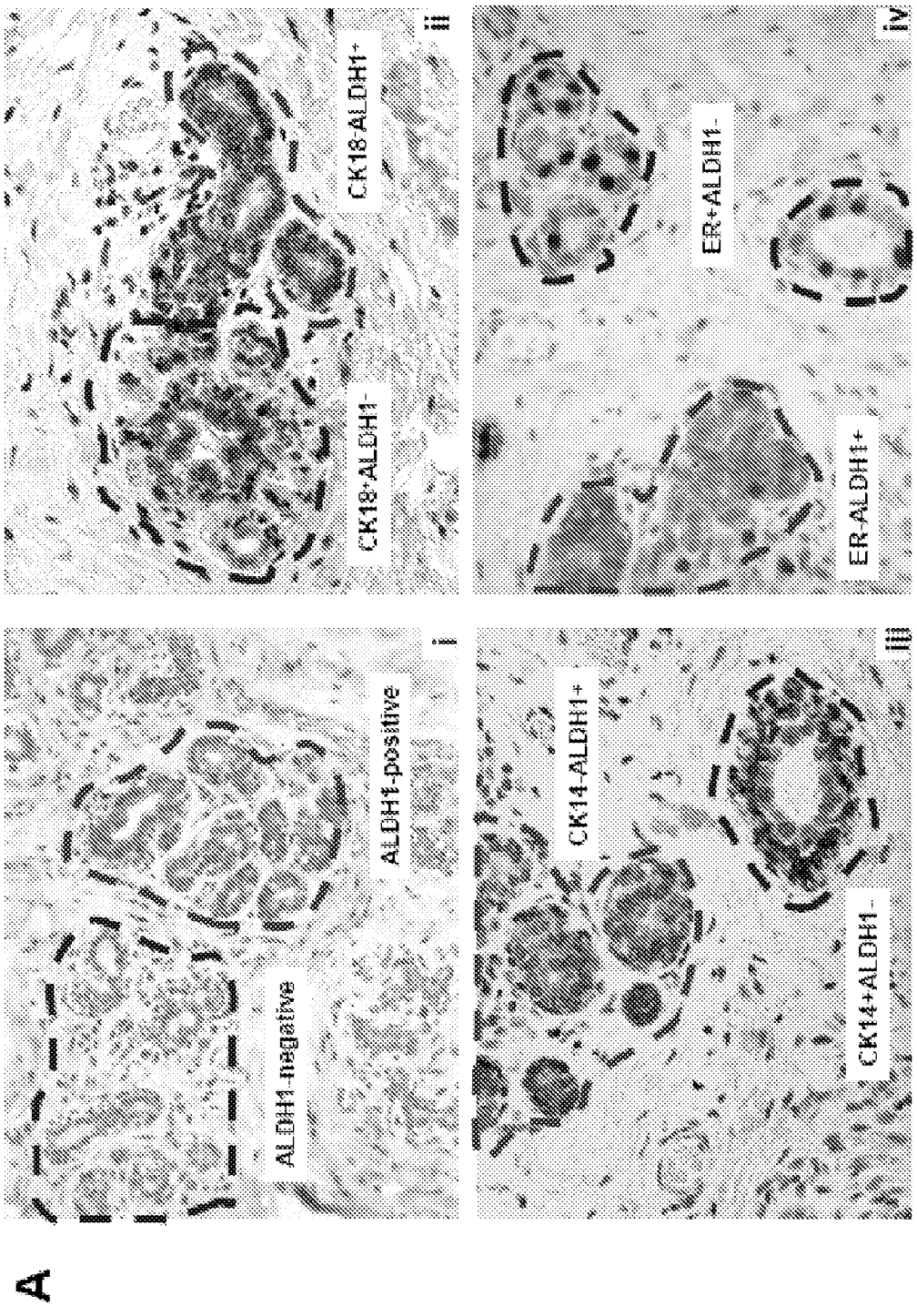
FIG. 12 shows that stem/progenitor cell expansion in BRCA1 mutation carriers is associated with LOH at the BRCA1 locus. A. Immunostaining for ALDH1 (i, red staining) was performed in samples obtained from prophylactic mastectomy specimens of women with confirmed BRCA1 mutations. Foci of ALDH1-positive cells comprising entire acini were detected (red circle). Double staining with ALDH1 (i, red staining) and CK18 (ii, brown staining), or CK14 (iii, brown staining), or ER (iv, brown staining) of normal breast epithelium from BRCA1 carrier patients showed an absence of expression in the ALDH1-positive acini (red circles) of CK18, and ER, and a reduced expression of CK14 whereas ALDH1-negative acini (blue circles) are composed of a continuous outer layer of CK14-positive myoepithelial cells surrounding an inner layer of CK18-positive and ER-positive epithelial cells. B. LOH analysis at the BRCA1 locus in ALDH1-positive acini versus ALDH1-negative acini. ALDH1-positive and adjacent ALDH1-negative lobules were isolated using laser capture microdissection. Extracted DNA from each microdissected sample was analyzed for four microsatellites in and telemeric to BRCA1 loci (D17S855, D17S1323, D17S1325, D17S806). In each of the four BRCA1 mutation carrier patients analyzed, LOH at the BRCA1 locus was demonstrated in at least one of the BRCA1 microsatellites markers in ALDH1-positive acini but not in ALDH1 negative acini. (LOH: Loss of Heterozygocity, ROH: Retention of Heterozygocity, NI: Noninformative)
Figure 12:
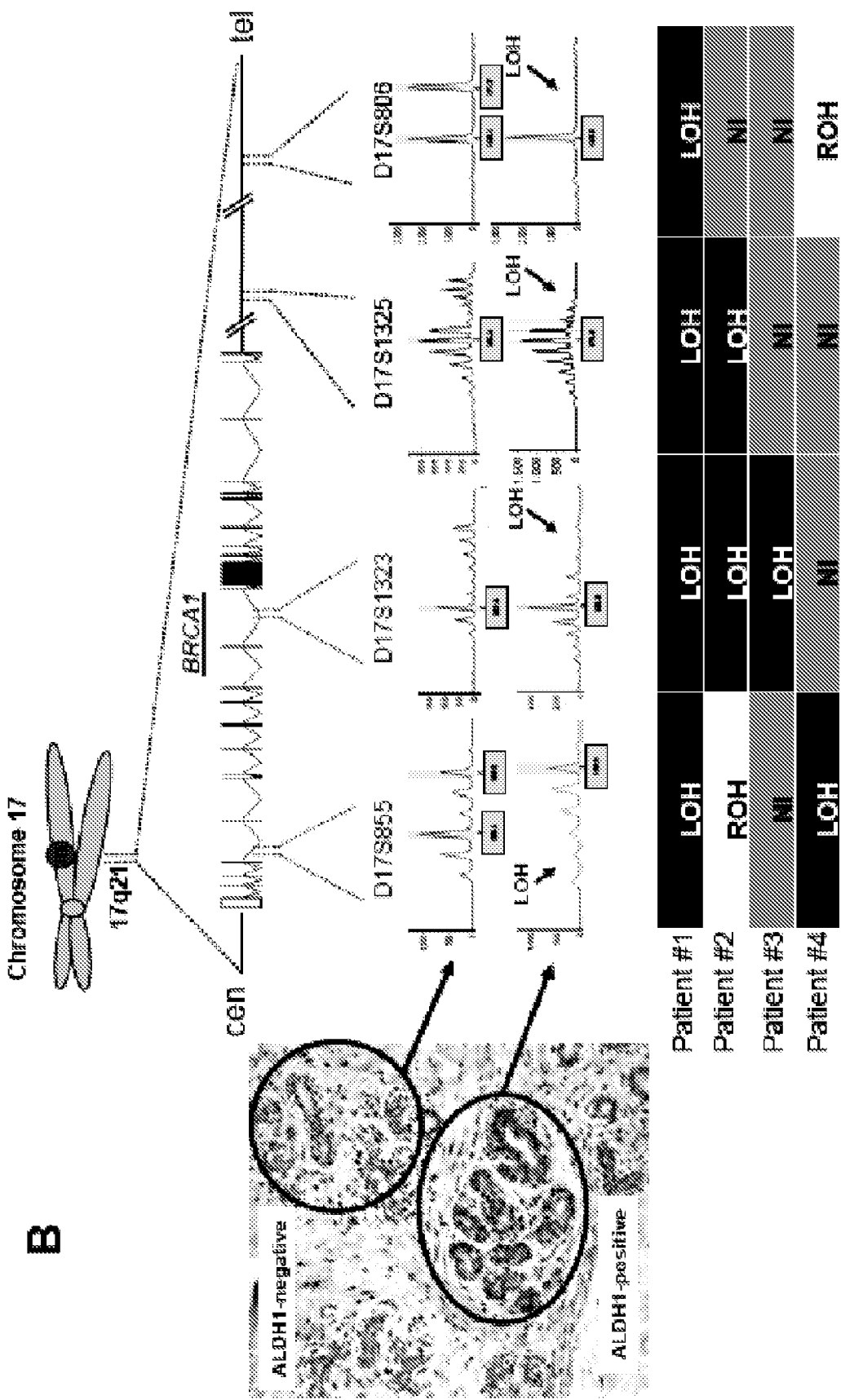

In order to further determine the clinical relevance of the in vitro and mouse model studies, the expression of the stem cell maker ALDH1 and ER was examined in breast tissue obtained from 13 women with documented deleterious BRCA1 germline alterations (mutations). These were compared to breast tissue obtained from reduction mammoplasties in 22 normal breast samples from patients with no family history of breast cancer. As shown in FIG. 12A, foci of ALDH1-positive cells were detected composed of entire acini in 5 out of 13 breast tissue samples obtained from BRCA1 mutation carriers. No such lobules were found in any of the control samples in which only a rare ALDH1-positive cell was found at areas of ductal branching. Cells expressing the stem/progenitor marker ALDH1 were morphologically normal but were negative for expression of the epithelial cell marker CK18 (FIG. 12A). These ALDH1-positive clusters also demonstrated reduced expression of CK14 and marked reduced expression of estrogen receptor (FIG. 12A).

While not necessary to understand to practice the present invention, it is believed that the ALDH1-positive lobules in BRCA1 mutation carriers resulted from a loss of BRCA1 expression in these lobules producing a block in stem/progenitor cell differentiation. Since it has been shown that tumors in BRCA1 mutation carriers demonstrate loss of heterozygosity (LOH) through loss of the normal BRCA1 allele (Albertsen et al. (1994) Nature genetics 7, 472-479), it was believed that there was a loss of the normal allele in ALDH1-positive but not the surrounding ALDH1-negative lobules. In order to assess this, laser capture micro-dissection was performed of ALDH1-positive lobules as well as adjacent ALDH1-negative lobules from samples obtained from four BRCA1 mutation carriers. DNA was extracted and analyzed for four microsatellite markers, two within the BRCA1 locus and two immediately telomeric. In each of the four BRCA1 mutation carriers, LOH at the BRCA1 locus was demonstrated in at least one of the BRCA1 polymorphic markers in ALDH1-positive but not in ALDH 1 negative lobules (FIG. 12B).

In summary, in vitro systems and mouse models demonstrate an important role for BRCA1 in regulating the differentiation of ALDH1-positive/ER-negative stem/progenitor cells into ER-positive epithelial cells. In BRCA1 mutation carriers, loss of the normal BRCA1 allele is associated with the development of lobules characterized by expression of the stem/progenitor marker ALDH1 with concomitant lack of expression of epithelial differentiation markers and ER. Recently using an MMTV-Cre;Brca1fl1/fl1p53f5&6/f5&6 model it has been suggested that progesterone plays a role in carcinogenesis in BRCA1 knockout mice (Poole et al. (2006) Science 314(5804), 1467-1470). In this model, unlike in the human situation, BRCA1 knock-out tumors expressed estrogen and progesterone receptors. In contrast, when BRCA1 was knocked out in more primitive basal cells using a K14cre; Brca1F/+;p53F/F construct this resulted in the generation of ER-negative/PR-negative tumors (Liu et al. (2007) PNAS104, 12111-12116). This demonstrates that BRCA1 associated tumor phenotype is dependent on the state of differentiation of cells in which BRCA1 function is lost and suggests that in human breast cancer this occurs in primitive stem/progenitor cells.

Taken together, this Example indicates that loss of BRCA1 function results in blocked epithelial differentiation with expansion of the undifferentiated stem/progenitor cell compartment. Since BRCA1 also functions in DNA repair and in maintaining chromosome stability, while not necessary to understand to practice the present invention, it is believed that loss of BRCA1 function produces genetically unstable stem/progenitor cells which serve as prime targets for further carcinogenic events including p53 mutations. This Examples lends support to the "cancer stem cell hypothesis" by indicating that dysregulation of stem cell self-renewal and differentiation may initiate hereditary as well as sporadic basal-like breast carcinomas, a portion of which are also characterized by loss of BRCA1 expression (Turner et al., (2006) Oncogene 25(43), 5846-5853). Furthermore, the ability to detect expanded stem cell clusters in histologically normal tissue from BRCA1 carriers may be used to identify women at particularly high risk for subsequent development of breast cancer.

All publications and patents mentioned in the above specification are herein incorporated by reference. Various modifications and variations of the described method and system of the invention will be apparent to those skilled in the art without departing from the scope and spirit of the invention. Although the invention has been described in connection with specific some embodiments, it should be understood that the invention as claimed should not be unduly limited to such specific embodiments. Indeed, various modifications of the described modes for carrying out the invention which are obvious to those skilled in the relevant fields are intended to be within the scope of the following claims.

We claim:
1. A method of detecting solid tumor stem cells in a subject and treating the subject based thereon, comprising;
   a) obtaining a solid tumor tissue sample from the subject, wherein the solid tumor tissue sample comprises breast cancer or colon cancer cells;
   b) determining if said solid tumor tissue sample contains solid tumor stem cells based on the presence of ALDH1 expression in said solid tumor tissue sample; and
   c) treating the subject with a therapy that selectively targets the solid tumor stem cells.
2. The method of claim 1, wherein said solid tumor tissue sample comprises breast cancer cells.
3. The method of claim 1, wherein said solid tumor tissue sample comprises colon cancer cells.
4. The method of claim 1, wherein said solid tumor tissue sample comprises inflammatory breast cancer cells.
5. The method of claim 1, wherein said solid tumor tissue sample is a paraffin embedded sample.
6. The method of claim 1, further comprising c) determining if said solid tumor tissue sample contains low levels of BRCA1 expression.
7. The method of claim 1, wherein said therapy that selectively targets the solid tumor stem cells comprises stimulating an immune response to a solid tumor stem cell.

* * * * *